(12) United States Patent
Babu et al.

(10) Patent No.: US 7,560,434 B2
(45) Date of Patent: Jul. 14, 2009

(54) AZA NUCLEOSIDES, PREPARATION THEREOF AND USE AS INHIBITORS OF RNA VIRAL POLYMERASES

(75) Inventors: Yarlagadda S. Babu, Birmingham, AL (US); Pooran Chand, Birmingham, AL (US); Ajit K. Ghosh, Birmingham, AL (US); Pravin L. Kotian, Hoover, AL (US); V. Satish Kumar, Birmingham, AL (US)

(73) Assignee: BioCryst Pharmaceuticals, Inc., Birmingham, AL (US)

( * ) Notice: Subject to any disclaimer, the term of this patent is extended or adjusted under 35 U.S.C. 154(b) by 410 days.

(21) Appl. No.: 11/157,867

(22) Filed: Jun. 22, 2005

(65) Prior Publication Data
US 2007/0099942 A1 May 3, 2007

Related U.S. Application Data

(60) Provisional application No. 60/581,377, filed on Jun. 22, 2004.

(51) Int. Cl.
*A01N 43/04* (2006.01)
*A61K 31/70* (2006.01)

(52) U.S. Cl. .................... 514/23; 536/18.7; 536/29.2

(58) Field of Classification Search .............. None
See application file for complete search history.

(56) References Cited

FOREIGN PATENT DOCUMENTS

WO WO-03/100009 A2 12/2003

OTHER PUBLICATIONS

Evans et al. J. Med. Chem. (2003), vol. 46, pp. 3412-3423.*
Chern et al. J. Med. Chem. (1993), vol. 36, pp. 1024-1031.*
"Crystal Structures of *Giardia lamblia* Guanine Phosphoribosyltransferase at 1.75 Å,†,‡," Shi et al., *Biochemistry* 2000, 39, pp. 6781-6790.

* cited by examiner

*Primary Examiner*—Patrick T Lewis
(74) *Attorney, Agent, or Firm*—Connolly Bove Lodge & Hutz LLP

(57) ABSTRACT

Compounds represented by the formula:

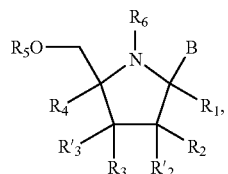

and pharmaceutically acceptable salts thereof and prodrugs thereof;

wherein $R_1$ is H, $CH_3$, $C_2H_5$, $C_3H_7$
$R_2$ is H, $CH_3$, $C_2H_5$, $C_3H_7$, $CH=CH_2$, $CH_2-OH$, $CH_2F$, $CF_3$
$R'_2$ is H, OH, $NH_2$, NH-alkyl, F, $N_3$, $OCH_3$, O—C(O)CH$(NH_2)$alkyl
$R_3$ is H, $CH_3$, $C_2H_5$, $C_3H_7$
$R'_3$ is H, OH, $NH_2$, NH-alkyl, F, $N_3$, $OCH_3$, O—C(O)CH$(NH_2)$alkyl
$R_4$ is H, $CH_3$, $C_2H_5$, $C_3H_7$
At least one of $R_2$, $R_3$, or $R_4$ has to be other than H, when X=NH in B

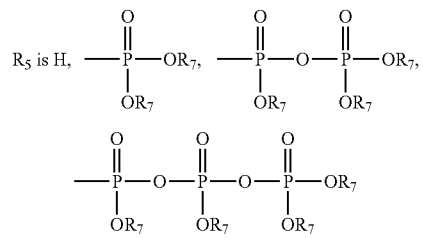

$R_6$ is H, $CH_3$, $C_2H_5$,

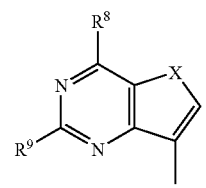

$R_7$ is selected from H, alkyl, alkenyl, aryl, acyloxyalkyl, and pivaloyloxyalkyl, aminoacids, $CH_2CH_2SC(O)$alkyl; and
B is represented by the following structure:

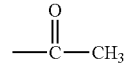

X is independently $NR^6$, O, S,
$R^8$ and $R^9$ independently is H, $NH_2$, OH, SH, F, Cl, Br, I, aryl, heterocycle, alkyl, alkene, alkyne, S-alkyl, S-aryl, S(O)-alkyl, $SO_2$-alkyl, $SO_2NH_2$, $SO_2NH$-alkyl, $SO_2NH$-aryl, NH-alkyl, NH-aryl, N(alkyl)$_2$, N(aryl)$_2$, O-alkyl, O-aryl, O-heterocycle, NH-$(CH_2)_n$-aryl, NH—C(O)-alkyl, NH—C(O)-aryl are useful for inhibiting viral RNA polymerases and treating patients suffering from diseases caused by various RNA viruses.

29 Claims, No Drawings

AZA NUCLEOSIDES, PREPARATION THEREOF AND USE AS INHIBITORS OF RNA VIRAL POLYMERASES

CROSS-REFERENCE TO RELATED APPLICATIONS

This Application claims priority under 35 USC 119(e) from U.S. Provisional patent application Ser. No. 60/581,377, filed Jun. 22, 2004, entitled AZA NUCLEOSIDES, PREPARATION THEREOF AND USE AS INHIBITORS OF RNA VIRAL POLYMERASES, entire disclosure of which is incorporated herein by reference.

DESCRIPTION

Technical Field

The present disclosure relates to certain nucleosides and particularly to nucleosides that are useful as inhibitors of viral RNA polymerases such as, but not limited to, hepatitis B, hepatitis C, Polio, Coxsackie A and B, Rhino, Echo, small pox, Ebola, and West Nile virus polymerases.

The present disclosure also relates to pharmaceutical compositions comprising the compounds of the present disclosure, as well as methods of using the compounds in inhibiting viral RNA polymerases and treating patients suffering from diseases caused by various RNA viruses.

The present disclosure also relates to a method for producing the compounds of the present disclosure.

BACKGROUND

Hepatitis C virus (HCV), as a particular example of an RNA virus, has infected an estimated 170 million people worldwide, leading to a major health crisis as a result of the disease. Indeed, during the next few years the number of deaths from HCV-related liver disease and hepatocellular carcinoma may overtake those caused by AIDS. Egypt is the hardest hit country in the world, with 23% of the population estimated to be carrying the virus; whereas, in the USA the prevalence of chronic infections has recently been determined to be around 1.87% (2.7 million persons). HCV infections become chronic in about 50% of cases. Of these, about 20% develop liver cirrhosis that can lead to liver failure, including hepatocellular carcinoma.

The NS5B region of HCV encodes a 65 KDa RNA-dependent RNA polymerase (RdRp) thought to be responsible for viral genome replication. RdRps function as the catalytic subunit of the viral replicase required for the replication of all positive-strand viruses. The NS5B protein has been well characterized, shown to possess the conserved GDD motif of RNA-dependent RNA polymerases and in vitro assay systems have been reported. Cellular localization studies revealed that NS5B is membrane-associated in the endoplasmic reticulum like NS5A, suggesting that those two proteins may remain associated with one another after proteolytic processing. Additional evidence suggests that NS3, NS4A and NS5B interact with each other to form a complex that function as part of the replication machinery of HCV.

The X-ray crystal structure of NS5B apoenzyme has now been determined and three very recent publications describe the unusual shape of the molecule. This unique shape for a polymerase, resembling a flat sphere, is attributed to extensive interactions between the fingers and thumb subdomains in such a way that the active site is completely encircled, forming a cavity 15 Å across and 20 Å deep. Modeling studies showed that the NS5B apoenzyme can accommodate the template-primer without large movement of the subdomains, suggesting that the structure is preserved during the polymerization reaction.

There are only a few reports of weak inhibitors of the polymerase. These include some nucleotide analogues, gliotoxin and the natural product cerulenin.

Accordingly, it would be desirable to develop inhibitors of RNA viral polymerases.

SUMMARY

The present disclosure relates to novel compounds and in particular, compounds that are represented by the formula:

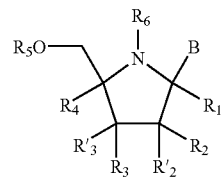

and pharmaceutically acceptable salts thereof and prodrugs thereof; and wherein $R_1$ is H, $CH_3$, $C_2H_5$, or $C_3H_7$;

$R_2$ is H, $CH_3$, $C_2H_5$, $C_3H_7$, $CH=CH_2$, $CH_2$—OH, $CH_2F$, or $CF_3$;

$R'_2$ is H, OH, $NH_2$, NH-alkyl, F, $N_3$, $OCH_3$, or O—C(O)CH($NH_2$)alkyl;

$R_3$ is H, $CH_3$, $C_2H_5$, or $C_3H_7$;

$R'_3$ is H, OH, $NH_2$, NH-alkyl, F, $N_3$, $OCH_3$, or O—C(O)CH($NH_2$)alkyl;

$R_4$ is H, $CH_3$, $C_2H_5$, $C_3H_7$; and

At least one of $R_2$, $R_3$, or $R_4$ is other than H, when X=NH in B;

$R_5$ is H, 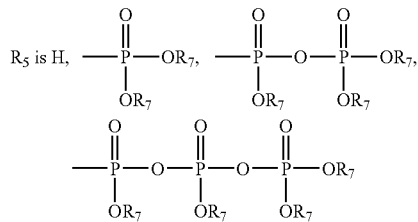

$R_6$ is H, $CH_3$, $C_2H_5$,

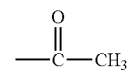

$R_7$ is selected from H, alkyl, alkenyl, aryl, acyloxyalkyl, pivaloyloxyalkyl, aminoacids, and $CH_2CH_2SC(O)$alkyl; and B is selected from the group consisting of 9-deazapurine derivatives.

To further illustrate, various of the purine derivatives, the following structure is taken as B

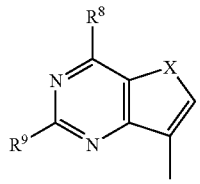

X is independently $NR^6$, O, or S; and
$R^8$ and $R^9$ independently is H, $NH_2$, OH, SH, F, Cl, Br, I, aryl, heterocycle, alkyl, alkene, alkyne, S-alkyl, S-aryl, S(O)-alkyl, $SO_2$-alkyl, $SO_2NH_2$, $SO_2NH$-alkyl, $SO_2NH$-aryl, NH-alkyl, NH-aryl, $N(alkyl)_2$, $N(aryl)_2$, O-alkyl, O-aryl, O-heterocycle, $NH$—$(CH_2)_n$-aryl, NH—C(O)-alkyl, or NH—C(O)-aryl.

The present disclosure also relates to a pharmaceutical composition comprising at least one of the above disclosed compounds and a pharmaceutical carrier.

A further aspect of the present disclosure relates to a method for inhibiting RNA viral polymerase in a patient by administering to the patient at least one of the above disclosed compounds in an amount effective for inhibiting RNA viral polymerase.

A still further aspect of the present disclosure relates to a method for treating a patient suffering from an RNA viral infection which comprises administering to said patient an effective amount of at least one of the above disclosed compounds.

Another the aspect of the present disclosure relates to a method for producing the above disclosed compounds.

Other and further objects, advantages and features of the present disclosure will be understood by reference to the following specification.

BEST AND VARIOUS MODES FOR CARRYING OUT DISCLOSURE

Compounds of the present disclosure are represented by the formula:

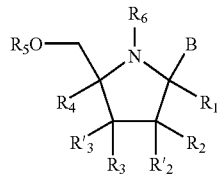

and pharmaceutically acceptable salts thereof and prodrugs thereof; and wherein $R_1$ is H, $CH_3$, $C_2H_5$, or $C_3H_7$;

$R_2$ is H, $CH_3$, $C_2H_5$, $C_3H_7$, $CH$=$CH_2$, $CH_2$—OH, $CH_2F$, or $CF_3$;

$R'_2$ is H, OH, $NH_2$, NH-alkyl, F, $N_3$, $OCH_3$, or O—C(O)CH($NH_2$)alkyl;

$R_3$ is H, $CH_3$, $C_2H_5$, or $C_3H_7$;

$R'_3$ is H, OH, $NH_2$, NH-alkyl, F, $N_3$, $OCH_3$, or O—C(O)CH($NH_2$)alkyl;

$R_4$ is H, $CH_3$, $C_2H_5$, or $C_3H_7$;

At least one of $R_2$, $R_3$, or $R_4$ has to be other than H, when X=NH in B;

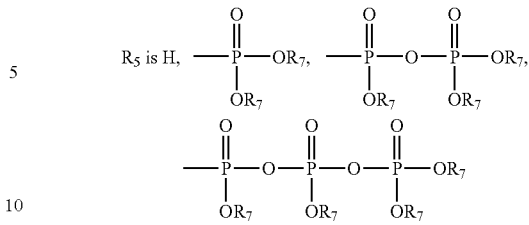

$R_6$ is H, $CH_3$, $C_2H_5$,

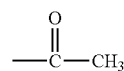

$R_7$ is selected from H, alkyl, alkenyl, aryl, acyloxyalkyl, pivaloyloxyalkyl, aminoacids, and $CH_2CH_2SC(O)$alkyl; and B is selected from the group consisting of 9-deazapurine derivatives.

To further illustrate, various of the purine derivatives, the following structure is taken as B

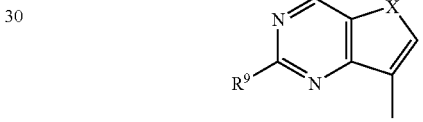

X is independently $NR^6$, O, or S;
$R^8$ and $R^9$ independently is H, $NH_2$, OH, SH, F, Cl, Br, I, aryl, heterocycle, alkyl, alkene, alkyne, S-alkyl, S-aryl, S(O)-alkyl, $SO_2$-alkyl, $SO_2NH_2$, $SO_2NH$-alkyl, $SO_2NH$-aryl, NH-alkyl, NH-aryl, $N(alkyl)_2$, $N(aryl)_2$, O-alkyl, O-aryl, O-heterocycle, $NH$—$(CH_2)_n$-aryl, NH—C(O)-alkyl, or NH—C(O)-aryl.

Definition of Terms

Listed below are definitions of various terms used to describe this invention. These definitions apply to the terms as they are used throughout this specification, unless otherwise limited in specific instances, either individually or as part of a larger group.

The terms "alkenyl" and "alkynyl" refer to straight or branched chain unsubstituted hydrocarbon groups typically having 2 to 8 carbon atoms.

The terms "substituted alkyl", "substituted alkenyl" or substituted alkynyl" refer to an alkyl, alkenyl or alkynyl group substituted by, for example, one to four substituents, such as halo, trifluoromethyl, trifluoromethoxy, hydroxy, alkoxy, cycloalkyloxy, heterocyclooxy, oxo, alkanoyl, aryloxy, alkanoyloxy, amino, alkylamino, arylamino, aralkylamino, cycloalkylamino, heterocycloamino, disubstituted amines in which the 2 amino substituents are selected from alkyl, aryl or aralkyl, alkanoylamine, aroylamino, aralkanoylamino, substituted alkanolamino, substituted arylamino, substituted aralkanoylamino, thiol, alkylthio, arylthio, aralkylthio, cycloalkylthio, heterocyclothio, alkylthiono, arylthiono, aralkylthiono, alkylsulfonyl, arylsulfonyl, aralkylsulfonyl, sulfonamido (e.g. $SO_2NH_2$), substituted sulfonamido, nitro, cyano, carboxy, carbamyl (e.g. $CONH_2$), substituted carbamyl (e.g. CONH alkyl, CONH aryl, CONH aralkyl or cases where there are two substituents on the nitrogen selected from alkyl, aryl or aralkyl), alkoxycarbonyl, aryl, substituted aryl, guanidino and heterocyclos, such as indolyl, imidazolyl, furyl, thienyl, thiazolyl, pyrrolidyl, pyridyl, pyrimidyl and the like. Where noted above, where the substituent is further substituted it will be with halogen, alkyl, alkoxy, aryl or aralkyl.

The term "halogen" or "halo" refers to fluorine, chlorine, bromine and iodine.

The term "aryl" refers to monocyclic or bicyclic aromatic hydrocarbon groups having 6 to 12 carbon atoms in the ring portion, such as phenyl, naphthyl, biphenyl and diphenyl groups, each of which may be substituted.

The term "aralkyl" or "alkylaryl" refers to an aryl group bonded directly through an alkyl group, such as benzyl or phenethyl.

The term "substituted aryl" or "substituted alkylaryl" refers to an aryl group or alkylaryl group substituted by, for example, one to four substituents such as alkyl; substituted alkyl, halo, trifluoromethoxy, trifluoromethyl, hydroxy, alkoxy, azido, cycloalkyloxy, heterocyclooxy, alkanoyl, alkanoyloxy, amino, alkylamino, aralkylamino, hydroxyalkyl, aminoalkyl, azidoalkyl, alkenyl, alkynyl, allenyl, cycloalkylamino, heterocycloamino, dialkylamino, alkanoylamino, thiol, alkylthio, cycloalkylthio, heterocyclothio, ureido, nitro, cyano, carboxy, carboxyalkyl, carbamyl, alkoxycarbonyl, alkylthiono, arylthiono, alkysulfonyl, sulfonamido, aryloxy and the like. The substituent may be further substituted by halo, hydroxy, alkyl, alkoxy, aryl, substituted aryl, substituted alkyl or aralkyl. "Substituted benzyl" refers to a benzyl group substituted by, for example, any of the groups listed above for substituted aryl.

The term "cycloalkyl" refers to optionally substituted, saturated cyclic hydrocarbon ring systems, preferably containing 1 to 3 rings and 3 to 7 carbons per ring which may be further fused with an unsaturated $C_3$-$C_7$ carbocyclic ring. Exemplary groups include cyclopropyl, cyclobutyl, cyclopentyl, cyclohexyl, cycloheptyl, cyclooctyl, cyclodecyl, cyclododecyl and adamantyl. Exemplary substituents include one or more alkyl groups as described above, or one or more groups described above as alkyl substituents.

The term "cycloalkenyl" refers to optionally substituted, unsaturated cyclic hydrocarbon ring systems, preferably containing 1 to 3 rings and 3-7 carbons per ring. Exemplary groups include cyclopentenyl and cyclohexenyl.

The term "alkyl" refers to straight or branched chain unsubstituted hydrocarbon groups of 1 to 20 carbon atoms, preferably 1 to 8 carbon atoms. The expression "lower alkyl" refers to unsubstituted alkyl groups of 1 to 4 carbon atoms. Alkyl groups may be substituted with halo (Cl, F, Br, I), OH, etc.

The term "aryl" refers to monocyclic or bicyclic aromatic hydrocarbon groups having 6 to 12 carbon atoms in the ring portion, such as phenyl, naphthyl, biphenyl and diphenyl groups, each of which may be substituted.

The term "acyl" refers to the residual moiety of a carboxylic acid group without the OH group of the acid and includes alkyl and acyl carboxylic acids. The alkyl group typically contains about 1-20 carbon atoms and more typically about 1-8 carbon atoms. The acyl group typically contains 6-12 carbon atoms. Examples of suitable acyl groups include acetyl and benzoyl.

Within the above-described definitions, certain embodiments are preferred. Preferred alkyl groups are lower alkyl groups containing 1 to about 8 carbon atoms, and more preferably 1 to about 5 carbon atoms, and can be straight, branched-chain or cyclic saturated aliphatic hydrocarbon groups.

Examples of suitable alkyl groups include methyl, ethyl and propyl. Examples of branched alkyl groups include isopropyl and t-butyl. An example of a suitable aralkyl group is phenethyl. Examples of suitable cycloalkyl groups typically contain 3-8 carbon atoms and include cyclopropyl, cyclobutyl, cyclopentyl and cyclohexyl. The aromatic or aryl groups are preferably phenyl and alkyl substituted aromatic groups (aralkyl) such as phenyl $C_{1-3}$ alkyl and benzyl.

Within the above-described definitions, certain embodiments are preferred. Preferred alkyl groups are lower alkyl groups containing 1 to about 8 carbon, and more preferably 1 to about 5 carbon atoms, and can be straight, branched-chain or cyclic saturated aliphatic hydrocarbon groups.

Examples of suitable alkyl groups include methyl, ethyl and propyl. Examples of branched alkyl groups include isopropyl and t-butyl. An example of a suitable alkylaryl group is phenethyl. Examples of suitable cycloalkyl groups typically contain 3-8 carbon atoms and include cyclopropyl, cyclobutyl, cyclopentyl and cyclohexyl. The aromatic or aryl groups are preferably phenyl or alkyl substituted aromatic groups (aralkyl) such as phenyl $C_{1-3}$ alkyl such as benzyl.

The terms "heterocycle", "heterocyclic" and "heterocyclo" refer to an optionally substituted, fully saturated or unsaturated, aromatic or nonaromatic cyclic group, for example, which is a 4 to 7 membered monocyclic, 7 to 11 membered bicyclic, or 10 to 15 membered tricyclic ring system, which has at least one heteroatom and at least one carbon atom in the ring. Each ring of the heterocyclic group containing a heteroatom may have 1, 2 or 3 heteroatoms selected from nitrogen atoms, oxygen atoms and sulfur atoms, where the nitrogen and sulfur heteroatoms may also optionally be oxidized and the nitrogen heteroatoms may also optionally be quaternized. The heterocyclic group may be attached at any heteroatom or carbon atom.

Prodrug forms of the compounds bearing various nitrogen functions (amino, hydroxyamino, amide, etc.) may include the following types of derivatives where each R group individually may be hydrogen, substituted or unsubstituted alkyl, aryl, alkenyl, alkynyl, heterocycle, alkylaryl, aralkyl, aralkenyl, aralkynl, cycloalkyl or cycloalkenyl groups as defined earlier.

(a) Carboxamides, —NHC(O)R
(b) Carbamates, —NHC(O)OR
(c) (Acyloxy)alkyl Carbamates, NHC(O)OROC(O)R
(d) Enamines, —NHCR($=CHCO_2R$) or —NHCR($=CHCONR_2$)
(e) Schiff Bases, —N=$CR_2$
(f) Mannich Bases (from carboximide compounds), $RCONHCH_2NR_2$ Preparations of such prodrug derivatives are discussed in various literature sources (examples are: Alexander et al., J. Med. Chem. 1988, 31, 318; Aligas-Martin et al. PCT WO pp/41531, p. 30). The nitrogen function converted in preparing these derivatives is one (or more) of the nitrogen atoms of a compound of the invention.

Prodrug forms of carboxyl-bearing compounds of the invention include esters (—$CO_2R$) where the R group corresponds to any alcohol whose release in the body through enzymatic or hydrolytic processes would be at pharmaceutically acceptable levels. Another prodrug derived from a carboxylic acid form of the invention may be a quaternary salt type

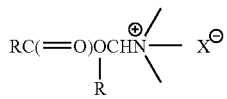

of structure described by Bodor et al. J. Med. Chem. 1980, 23, 469.

It is of course understood that the compounds of the present disclosure relate to all optical isomers and stereo-isomers at the various possible atoms of the molecule.

Pharmaceutically acceptable salts of the compounds of the present disclosure include those derived from pharmaceutically acceptable inorganic or organic acids. Examples of suitable acids include hydrochloric, hydrobromic, sulfuric, nitric, perchloric, fumaric, maleic, phosphoric, glycollic, lactic, salicyclic, succinic, toluene-p-sulfonic, tartaric, acetic, citric, methanesulfonic, formic, benzoic, malonic, naphthalene-2-sulfonic, trifluoroacetic and benzenesulfonic acids. Salts derived from appropriate bases include alkali such as sodium and ammonia.

Pursuant to the present disclosure, a study of the active site of HCV and other RNA polymerases as defined by x-ray crystallographic analysis indicates that many purine, pyrimidine and analogs thereof are tolerated in the part of the active site that binds the nucleic acid bases. It has also been determined according to the present disclosure that the part of the active site that binds the ribofuranose part of the nucleosides triphosphates can tolerate certain changes at the 2' and 3'-hydroxyls of the ribofuranose ring. The amino groups can be substituted with alkyl and aralkyl groups. Therefore, the above disclosed compounds have been identified as inhibitors of RNA polymerase pursuant to this disclosure. Such inhibitors with sufficient potency will block the function of this enzyme preventing viral replication providing potential drugs for the treatment of diseases resulting from these viruses, such as hepatitis C, small pox, Ebola virus, West Nile virus, Polio, Coxsackie A and B, Rhino, and Echovirus.

Synthesis of Compounds

The following abbreviations have been used throughout the synthesis.
MeOH methanol
DMAP 4-(dimethylamino)pyridine
Boc tert-butyloxycarbonyl
(Boc)$_2$O di-tert-butyl dicarbonate
CMA-80 chloroform:methanol:ammonium hydroxide (80:18:2)
CMA-50 chloroform:methanol:ammonium hydroxide (50:40:10)
RT room temperature
TBAF tetrabutylammonium fluoride
Troc 2,2,2-trichloroethyloxycarbonyl
TBDMS tert-butyldimethylsilyl
TBDMS-Cl tert-butyldimethylsilylchloride
TBDPS tert-butyldiphenylsilyl
TBDPS-Cl tert-butyldiphenylsilylchloride
TPP triphenylphosphine
DIPEA di-isopropylethylamine
Fmoc 9-fluorenylmethoxycarbonyl
Bredereck's reagent tert-butoxy-bis(N,N,-dimethylamino)methane
DBU 1,8-diazabicyclo[5.4.0]undec-7-ene
m-CPBA m-chloroperbenzoic acid
LDA lithium diisopropylamide
Tr triphenylmethyl
Tr-Cl triphenylmethyl chloride
DEAD diethylazodicarboxylate
TFA trifluoroacetic acid
PTSA p-toluenesulfonic acid

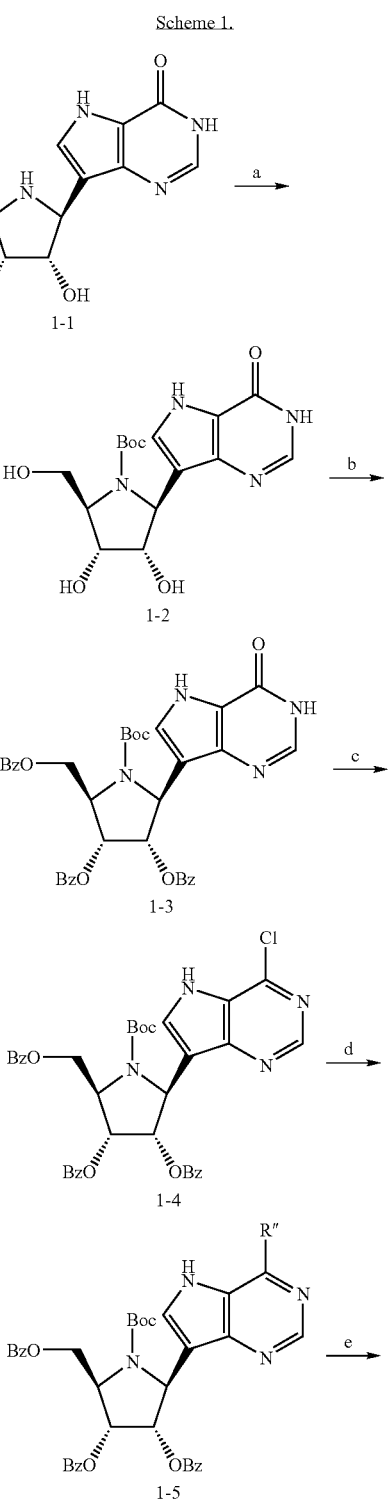

Scheme 1.

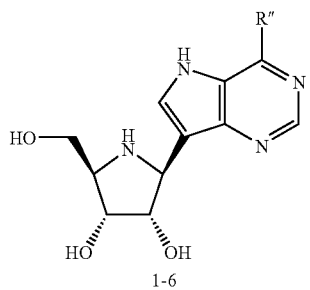

1-6 a. R″ = NHOCH₃
b. R″ = N(CH₃)NH₂
c. R″ = N(C₂H₅)NH₂
d. R″ = N(CH₃)₂

Reagents: a. (Boc)₂O, NEt₃, DMAP; b. BzCl, DMAP, Py; c. POCl₃, benzyl triethylammonium chloride, N,N-dimethylaniline, CH₃CN; d. methoxylamino hydrocloride, DIPEA, NaOH, MeOH; methyl hydrazine, EtOH, CHCl₃, methanolic NH₃; ethyl hydrazine oxalate, DIPEA, methanolic ammonia; or dimethylamine, Et₃N, methanolic ammonia; e. conc. HCl, MEOH.

Scheme 2.

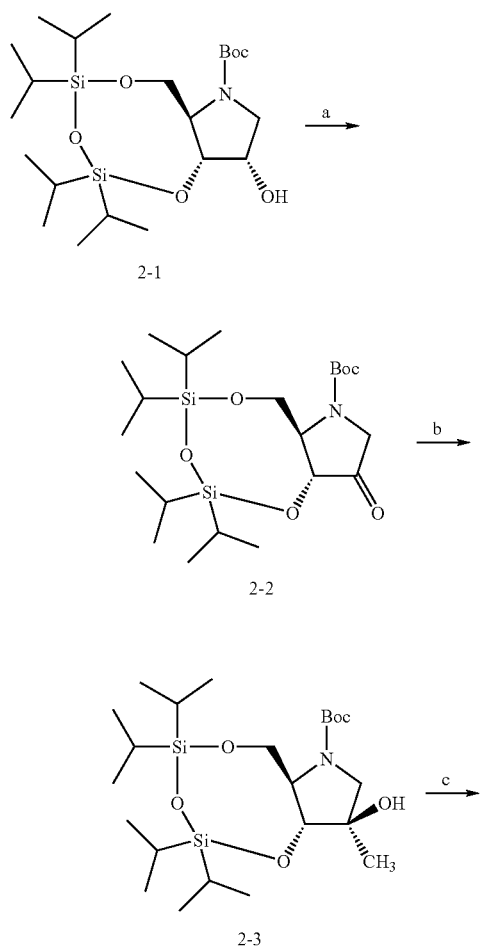

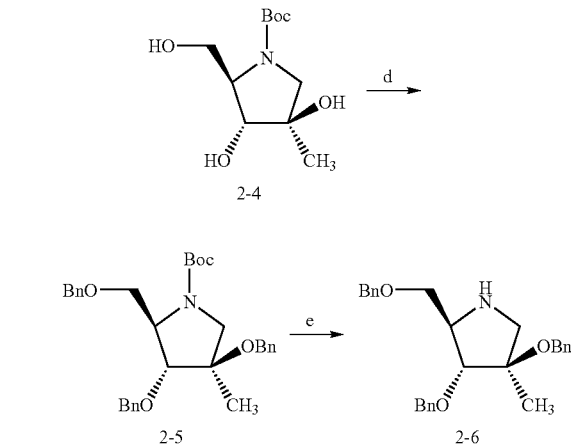

Reagents: a. CrO₃, py, Ac₂O; b. MeMgBr; c. TBAF; d. NaH, BnBr; e. TFA, THF/H₂O

Scheme 3.

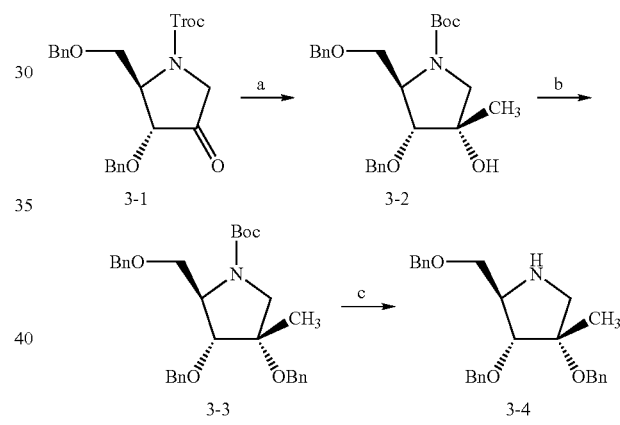

Reagents: a. TiCl₄, MeMgBr; b. NaH, BnBr; c. TFA, THF/H₂O

Scheme 4.

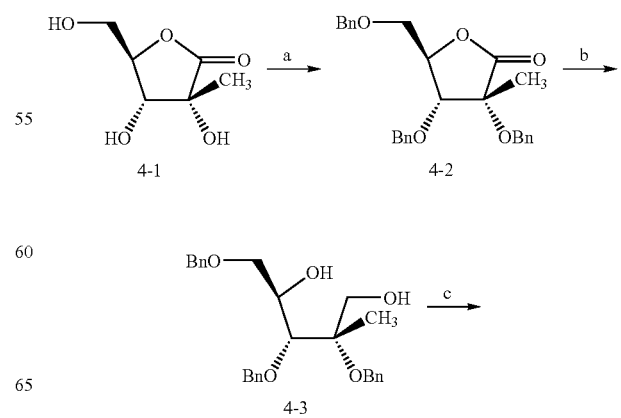

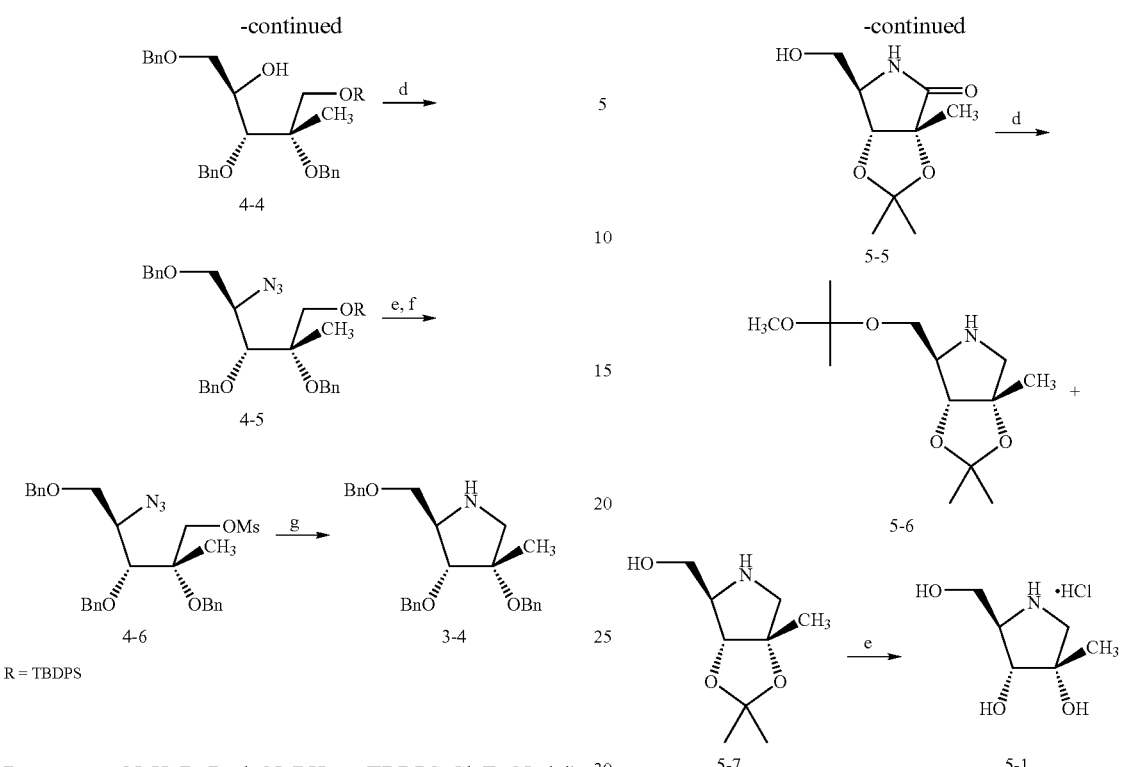
Reagents: a. NaH, BnBr; b. NaBH₄; c. TBDPS-Cl, Et₃N; d. i) TPP, DEAD, AcOH; ii) OH⁻; III) NaN₃; e. TBAF; f. MsCl, Et₃N; g. TPP, H₂O, THF.
Reagents: a. HCl, MeMOH, Pd/C, H₂; b. i) HCl, MeOH; ii) DIPEA; c. 2,2-dimethoxypropane, cat. p-TsOH, DMF; d. LAH; e. HCl.
Scheme 5.
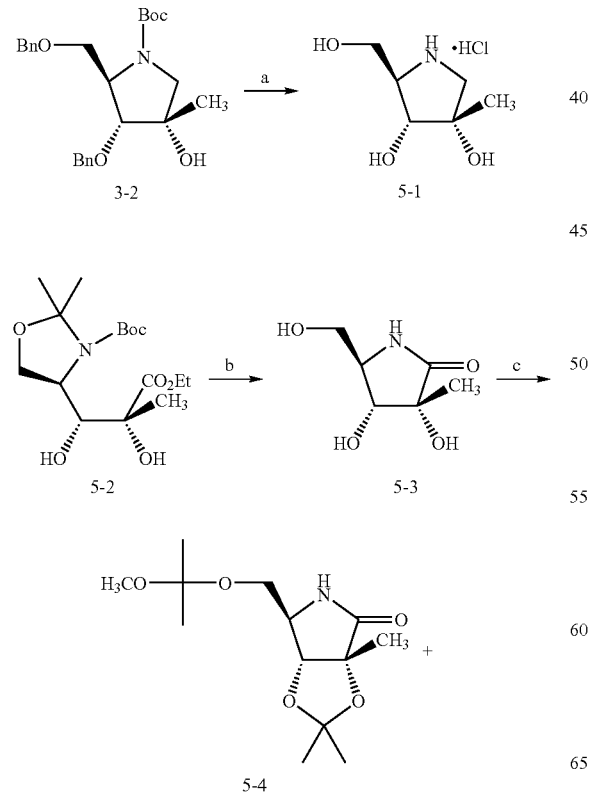
Scheme 6.
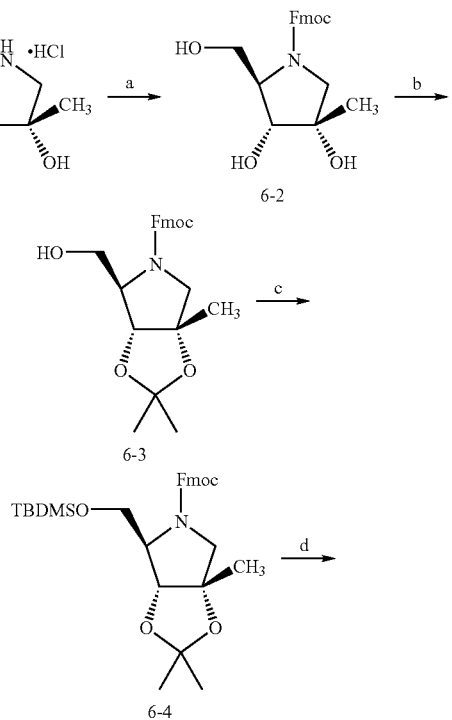

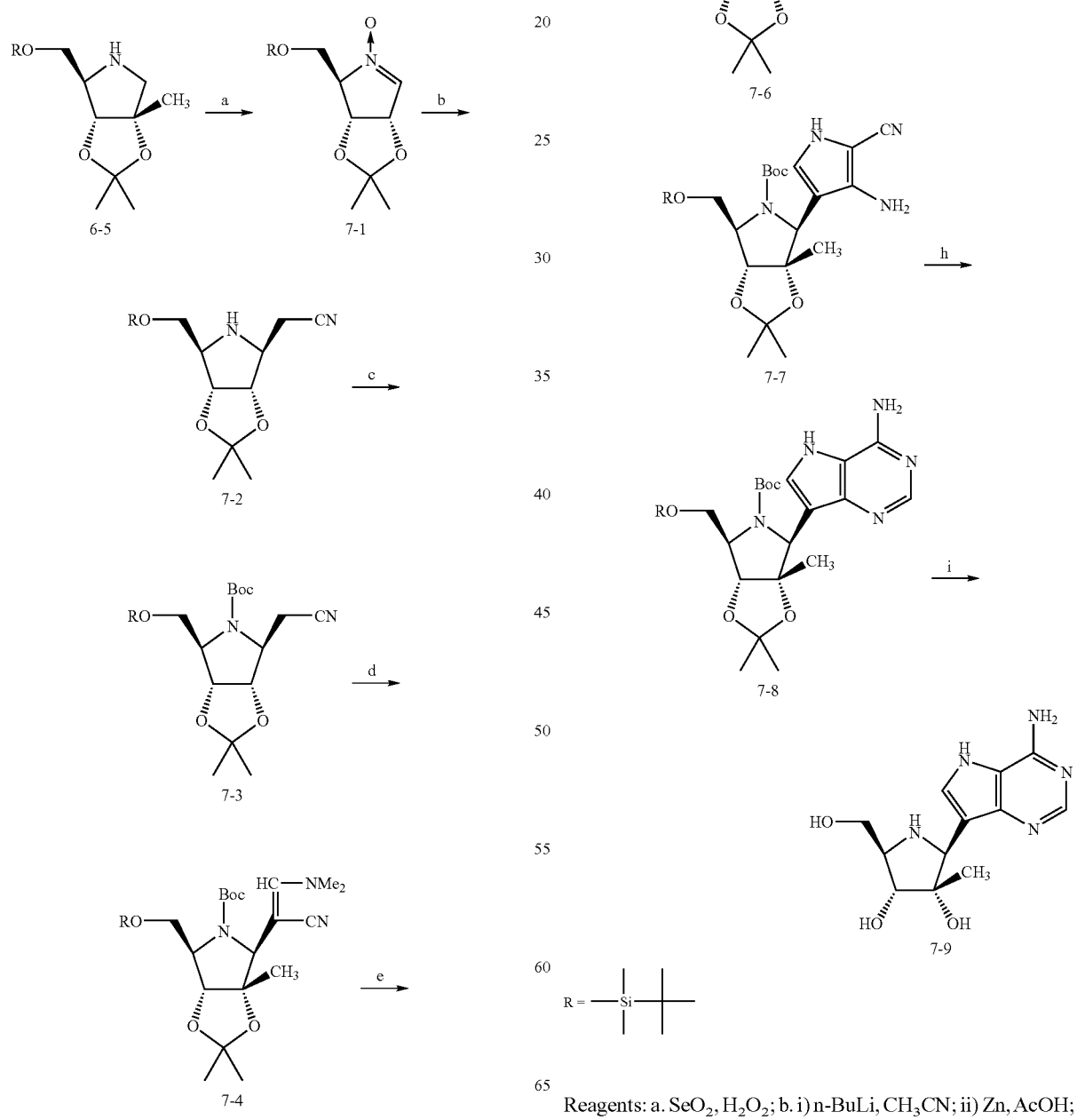
Reagents: a. FmocCl, DIPEA; b. Me$_2$CO, 2,2-dimethoxypropane, PTSA; c. TBDMSCl, imidazole; d. 20% piperdine.
Scheme 7.
Reagents: a. SeO$_2$, H$_2$O$_2$; b. i) n-BuLi, CH$_3$CN; ii) Zn, AcOH; c. (Boc)$_2$O, CHCl$_3$; d. tBuOCH(Nme$_2$)$_2$; e. THF, H$_2$O, AcOH; f. NH$_2$CH$_2$CN, CH$_3$COONa; g. DBU, ClCO$_2$Me; h. NH$_2$CH(=NH).AcOH; i. HCl, MeOH.
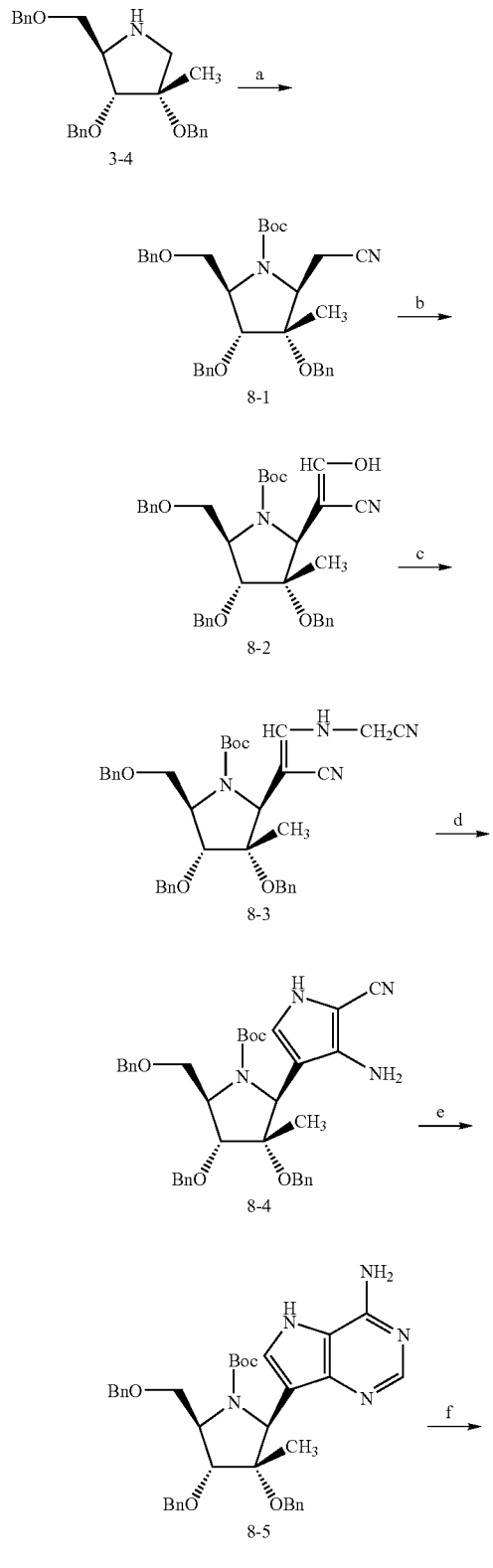
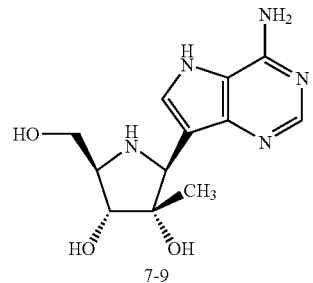
Reagents: Same as in scheme 7 except the last step, where BCl$_3$ has been used.
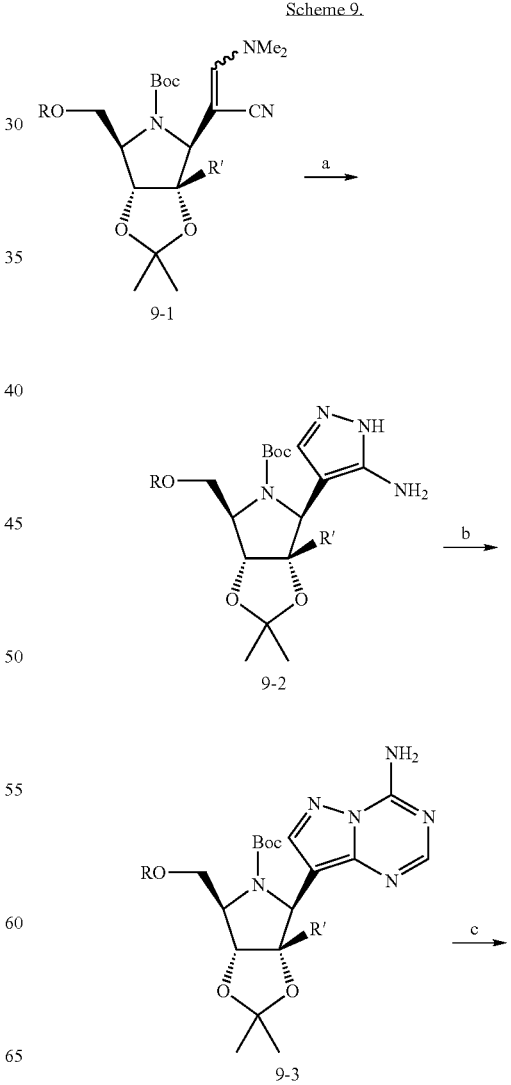

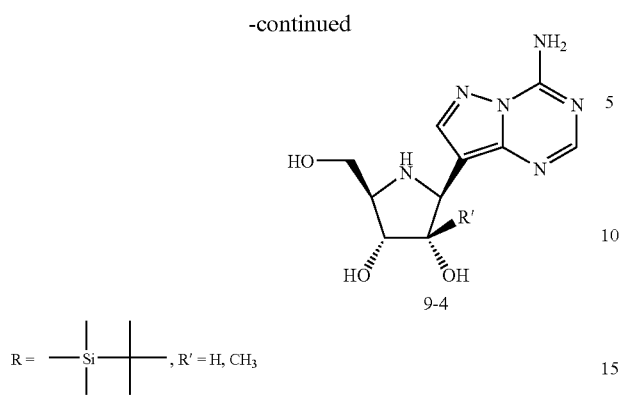

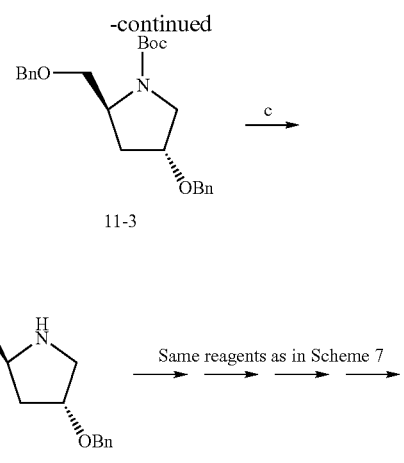

Reagents: a. NH$_2$—NH$_2$, NH$_2$—NH$_2$.HCl, MeOH; b. NC—N=CH—Oet; c. HCl, MeOH.

Scheme 10.

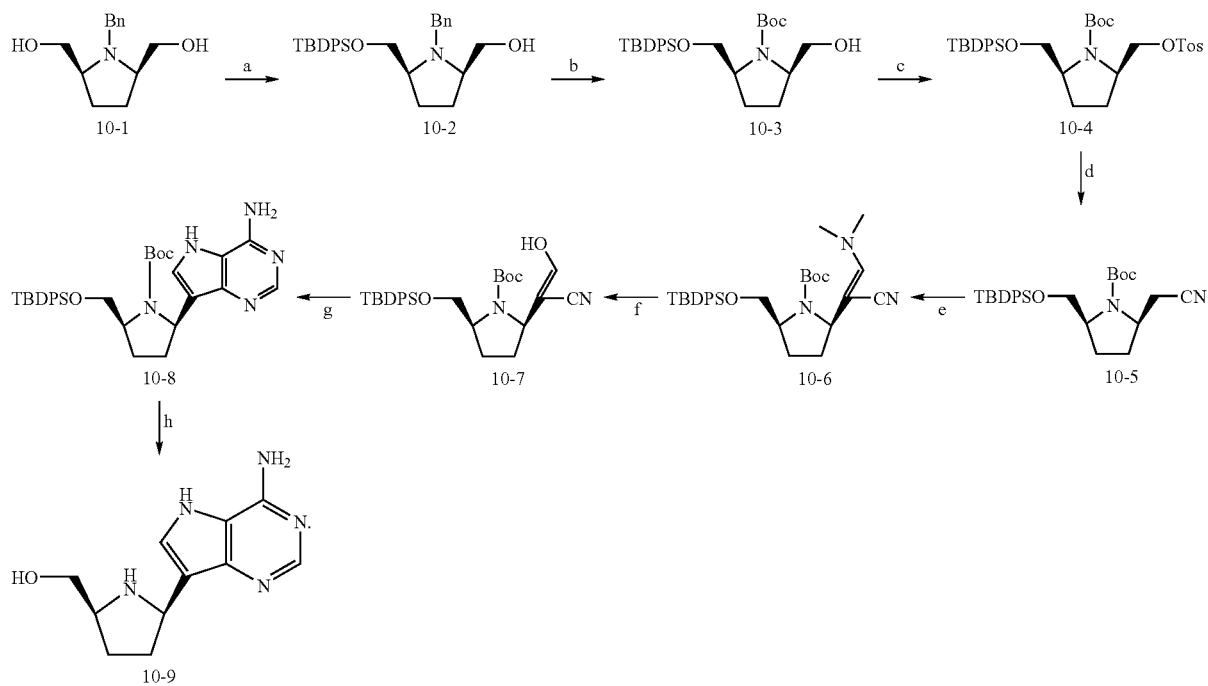

Reagents: a. TBDPSCl, pyridine; b. i) Pd(OH)$_2$, 100 psi H$_2$; ii) (Boc)$_2$O, CHCl$_3$; c. tosyl chloride, pyridine; d. NaCN, DMF; e. Bredereck's reagent, DMF; f. THF/AcOH/H$_2$O; g. i) amino acetonitrile.HCl, sodium acetate, MeOH; ii) ethyl chloroformate, DBU; iii) MeOH, Na$_2$CO$_3$; iv) formamidine acetate, EtOH; h. HCl, MeOH.

Scheme 11.

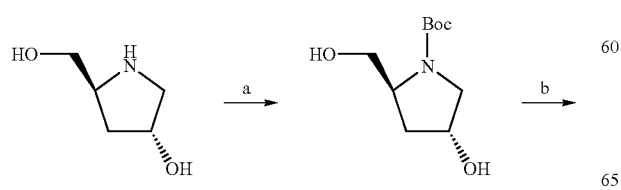

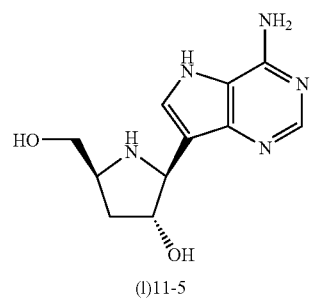

Reagents: a. (Boc)$_2$O, CHCl$_3$; b. benzylbromide, NaH; c. HCl.

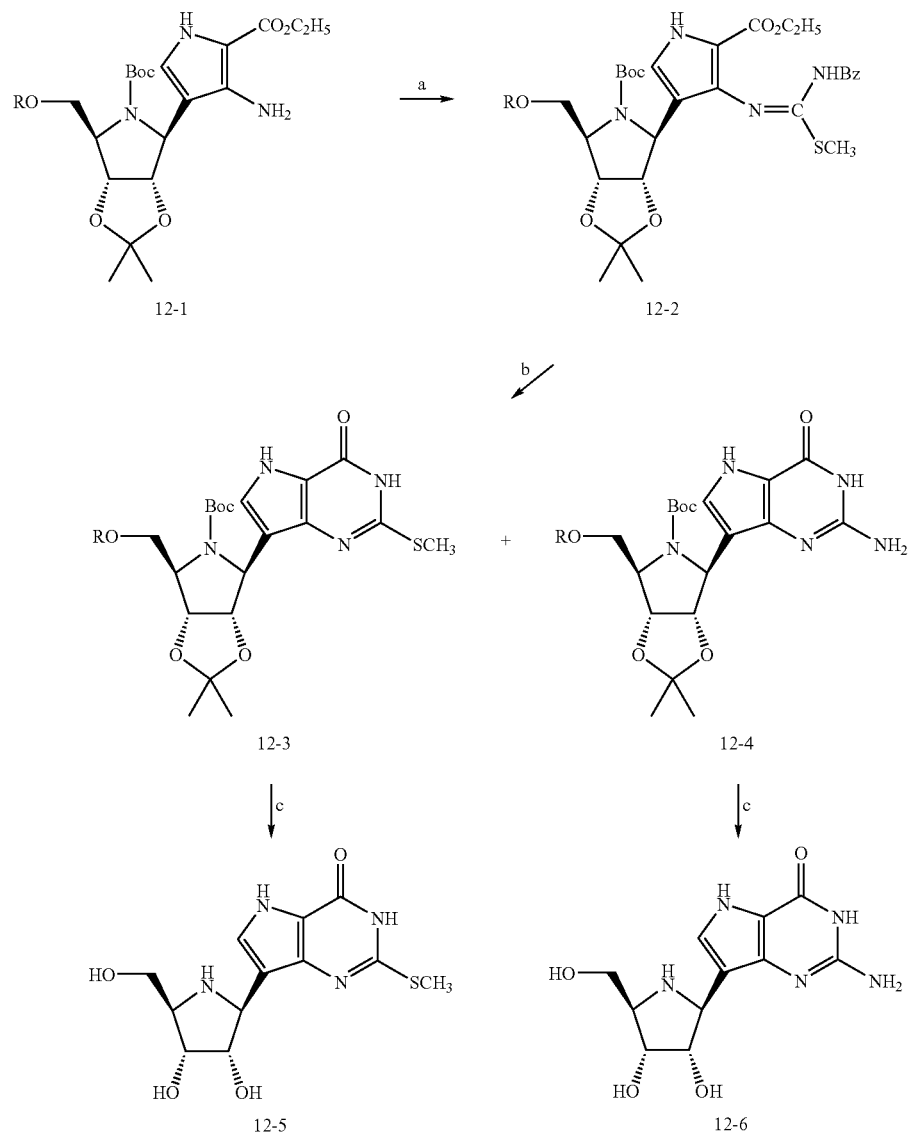
Reagents: a. i) $C_6H_5CONCS$, ii) DBU, $CH_3I$; b. $NH_3$, $CH_3OH$; c. HCl.
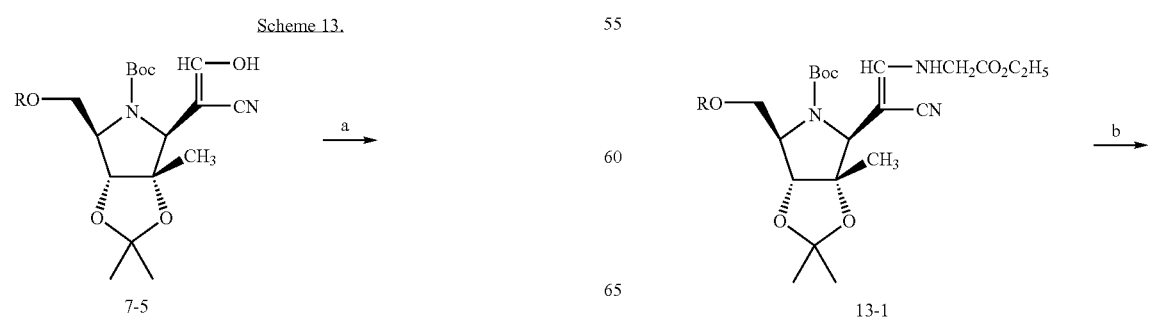

-continued
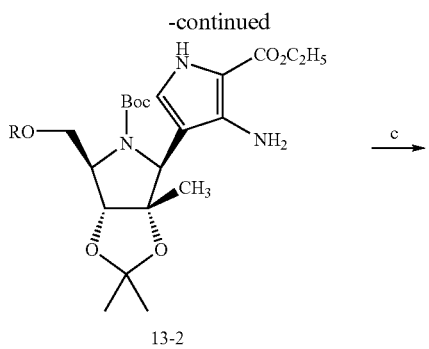
13-2
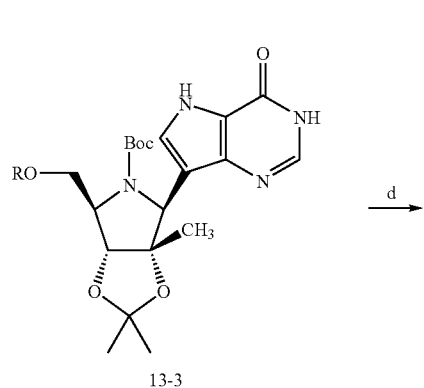
13-3
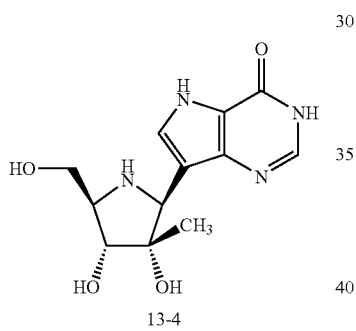
13-4
R = —Si—(CH3)2—C(CH3)3
Reagents: a. H₂N—CH₂CO₂Et.HCl, NaCOAc, MeOH; b. i) ClCO₂Bn, DBU; ii) H₂, Pd/C; c. H₂NCH=NH.AcOH, EtOH; d. HCl.
Scheme 14.
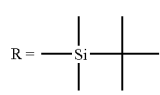
14-1
-continued
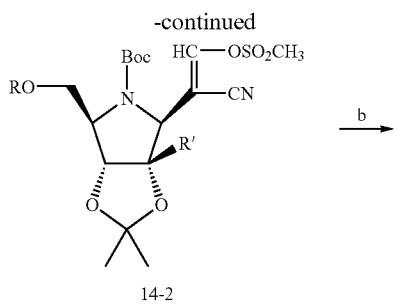
14-2
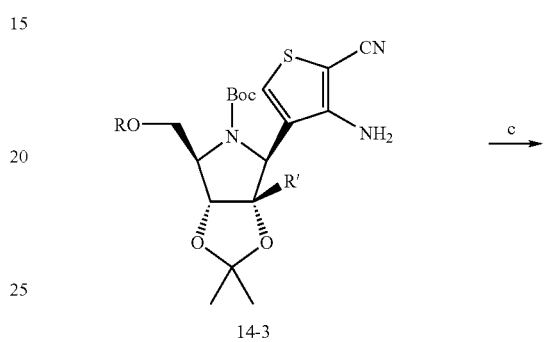
14-3
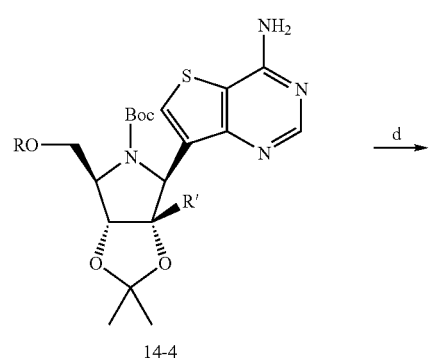
14-4
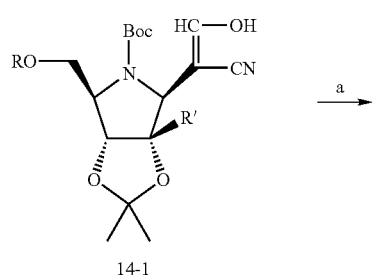
14-5
R = TBDMS
R' = H or CH₃
Reagents: a. CH₃SO₂Cl, Et₃N, CH₂Cl₂; b. H₃CC(O)S—CH₂CN, Na₂CO₃, EtOH; c. CH(=NH).NH₂.AcOH, EtOH; d. HCl.

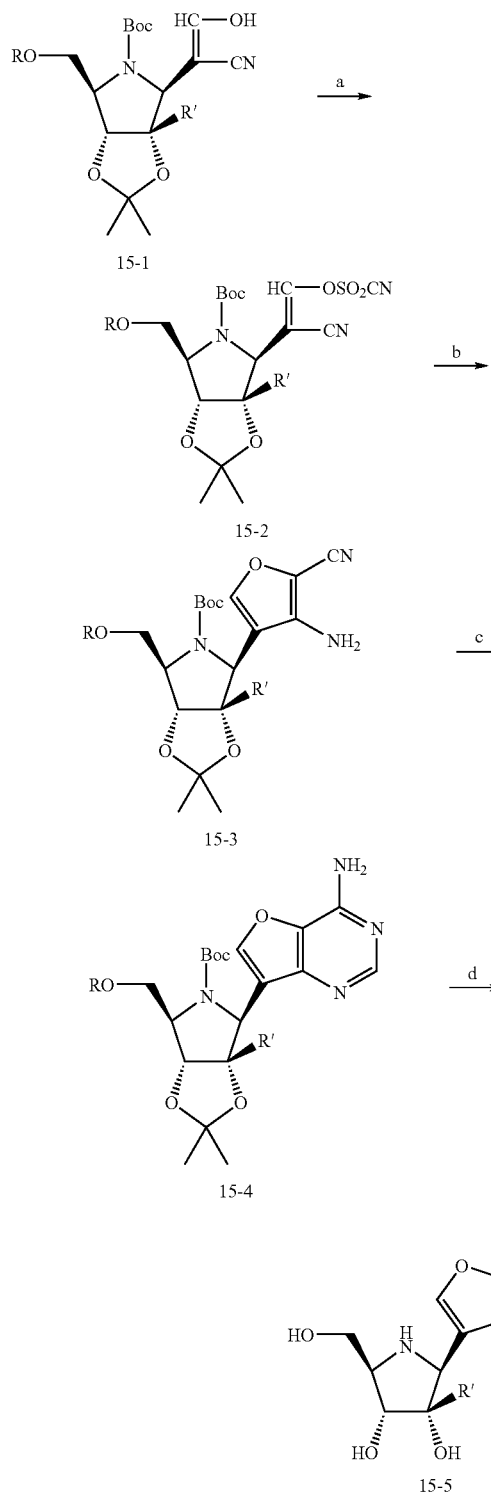

Scheme 15.

R=TBDMS

R'=H or CH₃

Reagents: a. ClCH₂CN, KF, 18-crown-6, DMF; b. L' CH(=NH).NH₂.AcOH, EtOH; d. HCl.

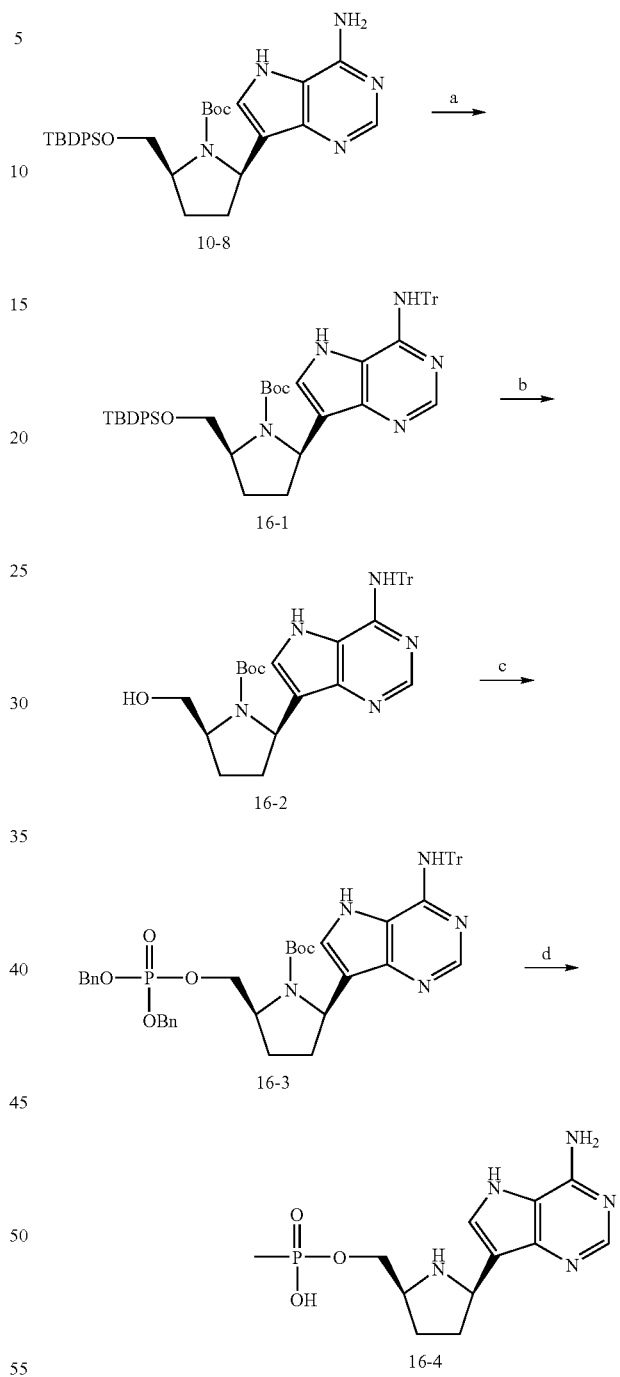

Scheme 16.

Reagents: a. TrCl, pyridine; b, TBAF, THF; c. i) dibenzyl diisopropyl phosphoramidate, tetrazole, THF; ii) mCPBA; d. i) H₂, Pd/C, MeOH; ii) CF₃CO₂H, CHCl₃.

The compounds of the present disclosure are prepared through Schemes 1-16 and the procedures are detailed in the following examples. The examples are not limited on the scope of the disclosure in any way. Those skilled in the art will appreciate that known variation of the conditions, reagents and processes of the following examples can be used to prepare these and other compounds of the present disclosure.

EXAMPLE 1

7-((2S,3S,4R,5R)-3,4-Dihydroxy-5-(hydroxymethyl)pyrrolidin-2-yl)-3H-pyrrolo[3,2-d]pyrimidin-4(5H)-one (Scheme 1, 1-1)

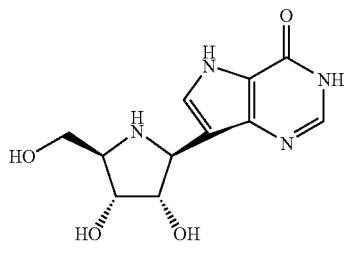

It is prepared following the procedures described in J. Org. Chem. (2001), 66, 5723-5730.

EXAMPLE 2

(2R,3R,4S,5S)-2-(Benzoyloxymethyl)-1-(tert-butoxycarbonyl)-5-(4-oxo-4,5-dihydro-3H-pyrrolo[3,2-d]pyrimidin-7-yl)pyrrolidine-3,4-diyl dibenzoate (Scheme 1, 1-3)

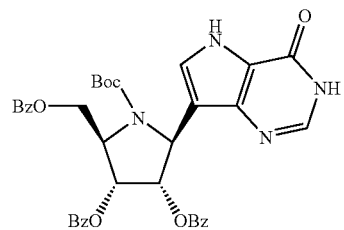

Step 1:

To a suspension of compound 1-1 in Scheme 1 (5 g, 16.52 mmol) in MeOH/H$_2$O (100 mL, 1:1 mixture) at RT is added triethylamine (3.345 g, 33.05 mmol) followed by DMAP (0.07 g, 0.57 mmol) and (Boc)$_2$O (4.46 g, 20.45 mmol) and stirred for 18 h. Additional (Boc)$_2$O (3.60 g, 16.52 mmol) in THF (25 mL) is added and the reaction mixture is stirred for an additional 2.5 h. The reaction mixture is concentrated to dryness and the residue is purified on silica gel by flash chromatography using CMA-80 in chloroform (50 to 100%) to CMA-50 which affords 5.92 g (98%) of 3,4-dihydroxy-2-hydroxymethyl-5-(4-oxo-4,5-dihydro-3H-pyrrolo[3,2-d]pyrimidin-7-yl)-pyrrolidine-1-carboxylic acid tert-butyl ester (1-2) as a colorless solid.

$^1$HNMR (DMSO-d$_6$): δ 11.89 (bs, 1H, DCl exchangeable), 7.73 (s, 1H), 7.29 (s, 0.3H), 7.20 (s, 0.7H), 5.54-5.50 (m, 0.7H, DCl exchangeable), 5.22-5.18 (m, 0.3H, DCl exchangeable), 4.99-4.87 (m, 1H), 4.71-4.69 (m, 1H, DCl exchangeable), 4.63-4.58 (m, 0.3H, DCl exchangeable), 4.51-4.47 (m, 0.7H, DCl exchangeable), 4.23-4.06 (m, 1H), 3.97-3.83 (m, 2H), 3.53-3.41 (m, 2H), 1.27 (s, 3H), 0.97 (s, 6H); MS (ES$^+$) 389.42 (M+23, 100%), MS (ES$^-$) 365.40 (M-1, 100%).

Step 2:

To a stirred solution of compound 1-2 from step 1 (5.85 g, 16.0 mmol) in pyridine (80 mL) is added benzoyl chloride (13.49 g, 96 mmol) and DMAP (0.05 g, 0.4 mmol) at RT. The reaction mixture is heated to 55° C. and then cooled to RT and stirred for 72 h. The reaction mixture is poured into saturated NaHCO$_3$ (400 mL) and ethyl acetate (250 mL) and stirred for 1.5 h. The reaction mixture is extracted with ethyl acetate (2×1 L) and the combined organic extracts are washed with cold HCl (0.1 N, 400 mL), saturated NaHCO$_3$ (1×200 mL), water (2×200 mL), and brine (1×250 mL) and dried (MgSO$_4$). After filtration, the filtrate is concentrated and the crude residue is purified on silica gel column by flash chromatography using ethyl acetate in hexanes (0 to 100%) to afford 6.35 g (58.5%) of 3,4-bis-benzoyloxy-2-benzoyloxymethyl-5-(4-oxo-4,5-dihydro-3H-pyrrolo[3,2-d]pyrimidin-7-yl)-pyrrolidine-1-carboxylic acid tert-butyl ester (1-3) as a gum.

$^1$HNMR (DMSO-d$_6$): δ 12.18 (d, J=2.4 Hz, 1H, D$_2$O exchangeable), 11.97 (J=3.9 Hz, 1H, D$_2$O exchangeable), 7.88-7.33 (m, 17H), 6.29 (bs, 1H), 6.04 (t, J=4.7 Hz, 1H), 5.36 (d, J=4.3 Hz, 1H), 4.87-4.78 (m, 2H), 4.51 (q, J=4.7 Hz, 1H), 1.47-1.25 (m, 9H); MS (ES$^+$) 701.31 (M+Na, 100%).

EXAMPLE 3

(2R,3R,4S,5S)-2-(Benzoyloxymethyl)-1-(tert-butoxycarbonyl)-5-(4-chloro-5H-pyrrolo[3,2-d]pyrimidin-7-yl)pyrrolidine-3,4-diyl dibenzoate (Scheme 1, 1-4)

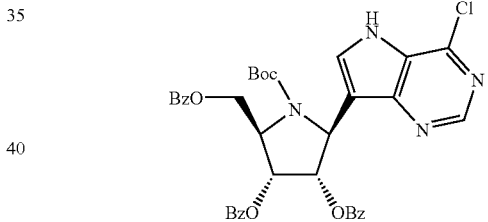

To a stirred solution of compound 1-3 (6 g, 8.84 mmol) in acetonitrile (18 mL) is added benzyltriethylammonium chloride (4.03 g, 17.69 mmol) and N,N-dimethylaniline (1.60 g, 13.28 mmol) at RT and the mixture is heated to 80° C. At 80° C., phosphorous oxychloride (8.14 g, 53.09 mmol) is added and stirring continues further at 80° C. for 10 min. After cooling, the mixture is concentrated and dichloromethane (50 mL) and ice cold water (20 mL) are added to the residue. The organic layer is separated and the aqueous layer is extracted with dichloromethane (2×25 mL). The combined organic layers are washed with saturated NaHCO$_3$ (15 mL), water (2×30 mL), and brine (1×25 mL), and dried (MgSO$_4$). After filtration, the filtrate is concentrated and the residue purified on silica gel by flash chromatography using ethyl acetate in hexanes (0 to 50%) to afford 5.3 g (86%) of the desired compound 1-4 as a colorless crystalline solid.

$^1$HNMR (DMSO-d$_6$): δ 12.51 (d, J=2.0 Hz, 1H, D$_2$O exchangeable), 8.59 (s, 1H), 7.98 (s, 1H), 7.87-7.32 (m, 15H), 6.43-6.32 (m, 1H), 6.14-6.10 (m, 1H), 5.46 (d, J=4.8 Hz, 1H), 4.92 (dd, J=11.8 and 6.9 Hz, 1H), 4.79 (dd, J=11.8 and 4.7 Hz, 1H), 4.59-4.54 (m, 1H), 1.45-1.14 (m, 9H); MS (ES$^+$) 719.22 (M+Na, 100%), MS (ES$^-$) 695.24 (M-1, 100%).

EXAMPLE 4

(2R,3R,4S,5S)-2-(Hydroxymethyl)-5-(4-(methoxyamino)-5H-pyrrolo[3,2-d]pyrimidin-7-yl)pyrrolidine-3,4-diol (1-6a, Scheme 1)

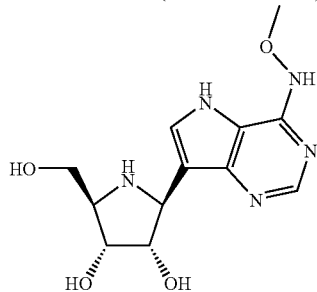

Step 1:

To a stirred solution of 1-4 in Scheme 1 (0.5 g, 0.71 mmol) in diisopropylethyl amine (5 mL) is added methoxyamine hydrochloride (0.29 g, 3.58 mmol) and the mixture is heated to 100° C. for 20 h. The reaction is not complete, so additional methoxyamine hydrochloride (0.87 g, 10.74 mmol) is added and again heated at reflux for 24 h. The reaction mixture is concentrated to dryness and the residue dissolved in MeOH (10 mL) and NaOH (10.5 mL, 1N) is added and stirred at RT for 24 h. After neutralization with HCl (2N), the reaction mixture is concentrated to dryness and the residue taken in chloroform (20 mL) and water (5 mL). The aqueous layer containing the compound is separated and concentrated and the residue is purified on silica gel using CMA-80 in chloroform (0 to 50%) to afford 39 mg of 4-dihydroxy-2-hydroxymethyl-5-(4-methoxyamino-5H-pyrrolo[3,2-d]pyrimidin-7-yl)-pyrrolidine-1-carboxylic acid tert-butyl ester (1-5a).

$^1$HNMR (DMSO-$d_6$+DCl): δ 8.64 (s, 1H), 7.83 (s, 1H), 4.81 (bs, 1H), 4.20-4.09 (m, 2H), 3.93 (s, 3H), 3.95-3.87 (m, 1H), 3.74-3.64 (m, 2H), 1.39 (s, 3H), 1.06 (s, 6H); MS (ES$^+$) 396.42 (M+1, 100%), MS (ES$^-$) 394.38 (M−1, 100%).

Step 2:

To a stirred solution of compound 1-5a from step 1 (46 mg, 0.11 mmol) in methanol (3 mL) is added concentrated HCl (0.075 mL, 0.91 mmol) and stirred at reflux for 2 h. After concentration, the residue is washed with ether, dissolved in methanol (2 mL), filtered through a small plug of cotton and concentrated to dryness to afford the desired target 1-6a (32 mg).

$^1$HNMR (DMSO-$d_6$+DCl): δ 8.68 (s, 1H), 8.07 (s, 1H), 4.82 (d, J=9.6 Hz, 1H), 4.44 (dd, J=9.4 and 5.1 Hz, 1H), 4.09 (dd, J=4.9 and 3.4 Hz, 1H), 3.90 (s, 3H), 3.7 (d, J=5.3 Hz, 2H), 3.56-3.52 (m, 1H); MS (ES$^+$) 296.42 (M+1, 100%).

EXAMPLE 5

(2R,3R,4S,5S)-2-(Hydroxymethyl)-5-(4-(1-methylhydrazinyl)-5H-pyrrolo[3,2-d]pyrimidin-7-yl)pyrrolidine-3,4-diol (1-6b, Scheme 1)

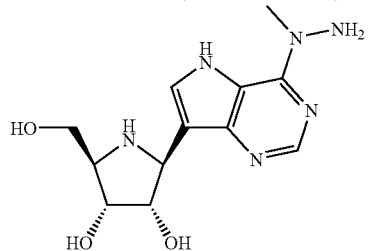

Step 1:

To a stirred solution of 1-4 in Scheme 1 (0.5 g, 0.71 mmol) in ethanol (15 mL) and chloroform (8 mL) is added methylhydrazine (0.31 g, 14.3 mmol) at RT and the reaction mixture is stirred for 3.5 h. The reaction mixture is concentrated to dryness, dissolved in saturated methanolic ammonia (25 mL), sealed in a steel bomb and stirred for 16 h at RT. After concentration, the residue is purified on silica gel column by flash chromatography using CMA-80 in chloroform to afford 165 mg (58.4%) of 3,4-dihydroxy-2-hydroxymethyl-5-[4-(N-methylhydrazino)-5H-pyrrolo[3,2-d]pyrimidin-7-yl]-pyrrolidine-1-carboxylic acid tert-butyl ester, 1-5b.

$^1$HNMR (DMSO-$d_6$+DCl): δ 8.43 (s, 1H), 7.55 (s, 1H), 4.65 (bs, 1H), 4.05-3.95 (m, 2H), 3.75 (dd, J=11.4 and 4.5 Hz, 1H), 3.58 (d, J=9.9 Hz, 2H), 3.44 (s, 3H), 1.26 (s, 3H), 0.93 (s, 6H); MS (ES$^+$) 395.49 (M+1, 100%), MS (ES$^-$) 393.46 (M−1, 100%).

Step 2:

To a stirred solution of compound 1-5b from step 1 (140 mg, 0.35 mmol) in methanol (3 mL) is added concentrated HCl (0.29 mL, 3.5 mmol) and the reaction mixture is heated at reflux for 2 h. After concentration, the residue is washed with ether, dissolved in methanol (2 mL), filtered through a small plug of cotton, concentrated and dried to afford the desired target 1-6b (90 mg, 87.4%).

$^1$HNMR (DMSO-$d_6$+DCl): δ 8.40 (s, 1H), 7.70 (s, 1H), 4.60 (d, J=9.4, 1H), 4.21 (dd, J=9.4 and 5.0 Hz, 1H), 3.87 (dd, J=4.7 and 3.7 Hz, 1H), 3.53 (d, J=6.0 Hz, 2H), 3.37-3.30 (m, 1H), 3.32 (s, 3H); MS (ES$^+$) 295.47 (M+1, 100%), 293.43 (M−1, 100%).

EXAMPLE 6

(2S,3S,4R,5R)-2-(4-(1-Ethylhydrazinyl)-5H-pyrrolo[3,2-d]pyrimidin-7-yl)-5-(hydroxymethyl)pyrrolidine-3,4-diol (1-6c, Scheme 1)

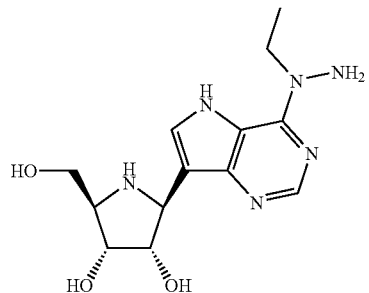

Step 1:

To a stirred solution of 1-4 in Scheme 1 (0.5 g, 0.71 mmol) in ethanol (15 mL) and chloroform (8 mL) are added ethylhydrazine oxalate (1.07 g, 7.17 mmol) and diisopropylethylamine (1.85 g, 14.34 mmol) at RT and stirred for 18 h. The reaction mixture is concentrated to dryness, dissolved in saturated methanolic ammonia (25 mL), sealed in a steel bomb and stirred for 16 h at RT. After concentration, the residue is purified on silica gel column by flash chromatography using CMA-80 in chloroform to afford 142 mg (48.5%) of 2-[4-(N-ethyl-hydrazino)-5H-pyrrolo[3,2-d]pyrimidin-7-yl]-3,4-dihydroxy-5-hydroxymethyl-pyrrolidine-1-carboxylic acid tert-butyl ester, 1-5c.

$^1$HNMR (DMOS-$d_6$+DCl): δ 8.55 (s, 1H), 7.69 (s, 1H), 4.77 (bs, 1H), 4.67-4.07 (m, 2H), 4.09 (q, J=7.1 Hz, 2H), 3.88

(dd, J=12.2 and 4.3 Hz, 1H), 3.75-3.65 (m, 2H), 3H), 1.37 (s, 3H), 1.30 (t, J=6.9 Hz, 3H), 1.05 (s, 6H); MS (ES+) 409.47 (M+1, 100%), MS (ES−) 407.46 (M−1, 100%).

Step 2:

To a stirred solution of the compound from step 1 (135 mg, 0.33 mmol) in methanol (15 mL) is added concentrated HCl (0.27 mL, 3.33 mmol) and the reaction mixture is heated at reflux for 2 h. After concentration, the residue is washed with ether, dissolved in methanol (2 mL), filtered through a small plug of cotton, concentrated and dried to afford the desired target 1-6c (100 mg, 97.4%).

$^1$HNMR (DMSO-d$_6$+DCl): δ 8.67 (s, 1H), 7.99 (s, 1H), 4.88 (d, J=9.6 Hz, 1H), 4.48 (dd, J=9.6 and 5.0 Hz, 1H), 4.19 (dd, J=5.0 and 3.4 Hz, 1H), 4.04 (q, J=6.9 Hz, 2H), 3.80 (d, J=4.5 Hz, 2H), 3.59 (dd, J=8.2 and 5.0 Hz, 1H), 1.33 (t, J=7.2 Hz, 3H); MS (ES+) 309.48 (M+1, 100%), 307.48 (M−1, 60%).

EXAMPLE 7

(2S,3S,4R,5R)-2-(4-(Dimethylamino)-5H-pyrrolo[3,2-d]pyrimidin-7-yl)-5-(hydroxymethyl)pyrrolidine-3,4-diol (Scheme 1, 1-6d)

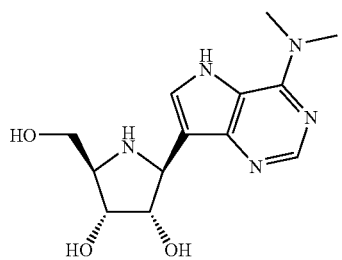

Step 1:

To a stirred solution of 1-4 in Scheme 1 (0.5 g, 0.71 mmol) in triethylamine (8 mL) is added dimethylamine (40%, 1.61 g, 14.34 mmol) at RT and stirred for 18 h. The reaction mixture is concentrated to dryness, dissolved in saturated methanolic ammonia (25 mL), sealed in a steel bomb and stirred for 16 h at RT. After concentration, the residue is purified on silica gel by flash chromatography using CMA-80 in chloroform to afford 29 mg (10.3%) of 2-(4-dimethylamino-5H-pyrrolo[3,2-d]pyrimidin-7-yl)-3,4-dihydroxy-5-hydroxymethyl-pyrrolidine-1-carboxylic acid tert-butyl ester, 1-5d.

MS (ES−) 392.42 (M−1, 100%).

Step 2:

To a stirred solution of compound 1-5d from step 1 (26 mg, 0.066 mmol) in methanol (3 mL) is added concentrated HCl (0.055 mL, 0.66 mmol) and the reaction mixture heated at reflux for 2 h. After concentration, the residue is washed with ether, dissolved in methanol (2 mL), filtered through a small plug of cotton, concentrated and dried to afford the desired target 1-6d (16 mg, 82.7%).

$^1$ HNMR (DMSO-d$_6$+DCl): δ 8.71 (s, 1H), 8.16 (s, 1H), 4.89 (d, J=9.6 Hz, 1H), 4.50 (dd, J=9.4 and 5.0 Hz, 1H), 4.15 (dd, J=5.0 and 3.3 Hz, 1H), 3.81 (d, J=5.2 Hz, 2H), 3.67-3.44 (m, 7H); MS (ES+) 294.46 (M+1, 100%).

EXAMPLE 8

(2R,3R,4R)-3,4-Bis(benzyloxy)-2-(benzyloxymethyl)-4-methylpyrrolidine (2-6, Scheme 2)

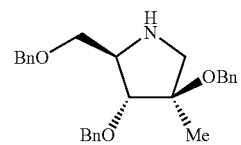

Step 1:

To a solution of CrO$_3$ (630 mg, 6.30 mmol), Ac$_2$O (0.59 mL, 6.3 mmol) and pyridine (1.01 mL, 12.60 mmol) in CH$_2$Cl$_2$ (30 mL) is added a solution of 3-hydroxy-5,5,7,7-tetraisopropyl-tetrahydro-4,6,8-trioxa-1-aza-5,7-disila-cyclopentacyclooctene-1-carboxylic acid tert-butyl ester, 2-1 (1.0 g, 2.10 mmol, prepared by following the method given in J. Med. Chem. (2003), 46, 3412-3423) at RT and the reaction mixture is stirred for 1 h. The reaction mixture is diluted with diethyl ether (100 mL), filtered through a short pad of Celite and the residue is washed with diethyl ether (2×50 mL). Combined ether solution is dried over MgSO$_4$, filtered and the filtrate is concentrated and the residue is purified on a silica gel column using hexanes:EtOAc (100:0 to 90:10) to provide 0.77 g (77%) of 2-2.

$^1$HNMR (CDCl$_3$): 4.53 (d, J=7.3 Hz, 1H), 4.15-4.35 (m, 2H), 3.76-3.90 (m, 3H), 1.48 (s, 9H), 0.95-1.14 (m, 28H); MS (ES−) 472.39 (M−H, 100%).

Step 2:

A solution of the above keto compound from step 1 (0.77 g, 1.63 mmol) in ether (50 mL) is cooled to −78° C. and MeMgBr (3.0 M in ether, 2.16 mL, 6.5 mmol) is added dropwise (10 min) at −78° C. The reaction mixture is then allowed to warm to −25 to −35° C. and stirred for 4 h and quenched with acetone (0.4 mL). The organic layer is separated and the aqueous layer extracted with ether (2×50 mL). The combined ether layers are washed with NH$_4$Cl (2N, 50 mL), dried over MgSO$_4$, filtered and the filtrate is evaporated to dryness to give 0.73 g of the desired compound, 2-3; MS (ES+) 512.45 (M+Na, 30%).

Step 3:

A solution of the compound from step 2 (0.72 g, 1.47 mmol) in THF (30 mL) is treated with TBAF (1.0 M in THF, 5.88 mL, 5.88 mmol) and the reaction mixture is stirred at RT for 18 h and evaporated to dryness. The residue is dissolved in EtOAc (2.0 mL) and purified on silica gel column using hexane:EtOAc:MeOH (80:20:0 to 50:50:7) to provide 0.214 g (59%) of 3,4-dihydroxy-2-hydroxymethyl-4-methyl-pyrrolidine-1-carboxylic acid tert-butyl ester, 2-4.

$^1$HNMR (DMSO): 5.13-5.18 (m, 1H), 5.02 (s, 1H), 4.84-4.92 (m, 1H), 3.34-3.84 (m, 4H), 3.20 (d, J=10.9 Hz, 1H), 3.12(d, J=10.9 Hz, 1H), 1.38 (s, 9H), 1.13 (s, 3H); MS (ES+) 270.50 (M+Na, 40%).

Step 4:

To a solution of the compound from step 3 (0.2 g, 0.81 mmol) in DMF (7 mL) is added NaH (60% dispersion in mineral oil, 161 mg, 4.04 mmol) at 0 to −5° C. and the reaction mixture is stirred at 0 to −5° C. for 15 min and then BnBr (0.83 g, 4.84 mmol) is added over a period of 10 min. The mixture is further stirred at RT for 6 h and neutralized with 25% aqueous AcOH. The mixture is diluted with water (50 mL) and extracted with EtOAc (3×50 mL). The combined organic layers are washed with water (1×50 mL), dried over MgSO$_4$, filtered and concentrated under vacuum. The residue is purified on a silica gel column using hexanes:EtOAc (100:0 to 90:10) to provide 0.304 g (73%) of the desired compound 2-5 as an oil.

$^1$HNMR (CDCl$_3$): 7.18-7.35 (m, 15H), 4.35-4.70 (m, 6H), 3.39-4.14 (m, 6H), 1.45 (s, 3H), 1.41 (s, 9H); MS (ES+) 540.11 (M+Na, 100%).

Step 5:

To a solution of the compound from step 4 (0.25 g, 0.48 mmol) in THF (2 mL) is added water (2 mL) and TFA (3.5 mL) and then heated at 75° C. for 2 h. The reaction mixture is concentrated under vacuum and then treated with saturated NaHCO$_3$ (50 mL), extracted with EtOAc (3×40 mL). The combined organic layers are washed with water (1×40 mL), dried over MgSO$_4$, filtered and concentrated under vacuum. The residue is purified on a silica gel column using hexanes:EtOAc:MeOH (80:20:0 to 50:50:5) to provide. 0.15 g (74%) of the product 2-6 as an oil.

$^1$HNMR (CDCl$_3$): 7.20-7.36 (m, 15H), 4.41-4.67 (m, 6H), 3.79 (d, J=5.4 Hz, 1H), 3.60 (dd, J=9.4 and 4.8 Hz, 1H), 3.52 (dd, J=9.4 and 5.0 Hz, 1H), 3.18-3.23 (m, 2H ), 2.79 (d, J=12.0 Hz, 1H), 1.93 (brs, 1H), 1.43 (s, 3H); MS (ES+) 418.43 (M+H, 100%).

EXAMPLE 9

(2R,3R,4S)-3,4-Bis(benzyloxy)-2-(benzyloxymethyl)-4-methylpyrrolidine (3-4, Scheme 3)

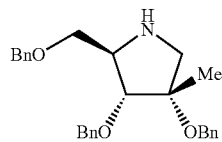

Step 1:

TiCl$_4$ (38 mL, 66 g, 345 mmol) is added dropwise at −78° C. to diethyl ether (1250 mL) under nitrogen over a period of 20 min. To the resultant yellow etherate is then added methyl magnesium bromide in ether. (3.0 M, 115 mL, 345 mmol) over a period of 25 min. and the reaction mixture is allowed to warm to −45° C., whereupon a solution of 3-benzyloxy-2-benzyloxymethyl-4-oxo-pyrrolidine-1-carboxylic acid 2,2,2-trichloro-ethyl ester, 3-1 (42 g, 86.28 mmol, prepared by following the method given in J. Med. Chem. (2003), 46, 3412-3423) in ether (250 mL) is added via cannula over a period of 35 min. The reaction mixture is further stirred at −30° C. to −10° C. for 3.5 h and quenched with NH$_4$Cl (2N, 100 mL) followed by water (500 mL). The organic layer is separated and the aqueous layer is extracted with ether (2×250 mL). Combined ether layers are dried over MgSO$_4$, filtered and the filtrate is concentrated. The residue is purified on a silica gel column using hexanes:CHCl$_3$:Et$_3$N (78:20:2) to provide 21.75 g of the desired compound. This compound (21.3 g, 42.36 mmol) is dissolved in acetic acid (425 mL) and treated with Zn dust (23 g, 351 mmol) and the mixture stirred for 16 h at RT. After filtration, AcOH is evaporated under reduced pressure and the remaining mass treated slowly with saturated NaHCO$_3$ (200 mL), extracted with CHCl$_3$ (3×150 mL), dried, filtered and the filtrate is concentrated. The residue is dissolved in dichloromethane (400 mL) and treated with (Boc)$_2$O (18.4 g, 84.76 mmol) and Et$_3$N (18 mL, 128 mmol). The reaction mixture is stirred for 16 h. After concentration, the residue is purified on a silica gel column using hexanes:CHCl$_3$:Et$_3$N (90:10:0 to 80:18:2) to provide 11.2 g of compound 3-2 as a thick gum.

$^1$HNMR (CDCl$_3$): 7.23-7.38 (m, 10H), 4.41-4.68 (m, 4H), 3.54-3.94 (m, 4H), 2.60-3.16 (m, 2H), 1.40-1.44 (m, 9H), 1.28 (s, 3H); MS (ES+) 450.56 (M+Na, 100%).

Step 2:

To a solution of the compound from step 1 (2.2 g, 5.14 mmol) in DMF (45 mL) is added NaH (60% dispersion in mineral oil, 411 mg, 10.29 mmol) at RT and the reaction mixture stirred for 15 min and then BnBr (1.25 mL, 10.29 mmol) is added over a period of 10 min and further stirred for 16 h. Additional NaH (411 mg, 10.29 mmol) and BnBr (1.25 mL, 10.29 mmol) are added as before and the reaction mixture is stirred at RT for 4 h. The mixture is neutralized with 25% aqueous AcOH, diluted with water (150 mL) and extracted with EtOAc (3×100 mL). The combined organic layers are washed with water (2×150 mL), dried over MgSO$_4$, filtered and the filtrate is concentrated. The residue is purified on a silica gel column using hexanes:EtOAc (100:0 to 90:10) to provide 1.75 g (66%) of product 3-3 as an oil.

$^1$HNMR (CDCl$_3$): 7.18-7.36 (m, 15H), 4.45-4.75 (m, 6H), 3.50-4.00 (m, 5H), 2.97-3.11 (m, 1H), 1.34-1.39 (s, 12H); MS (ES+) 540.50 (M+Na, 1.00%).

Step 3:

To a solution of the compound from step 2 (1.75 g, 3.38 mmol) in THF (15 mL) is added water (7 mL) and TFA (7 mL) and then heated at 75° C. for 2 h. The reaction mixture is concentrated under vacuum and then treated with saturated NaHCO$_3$ (100 mL) and extracted with EtOAc (3×75 mL). The combined organic layers are washed with water (1×100 mL), dried over MgSO$_4$, filtered and the filtrate is concentrated. The residue is purified on a silica gel column using hexanes:EtOAc:MeOH (70:30:0 to 50:50:5) to provide 1.07 g (76%) of product 34 as an oil.

$^1$HNMR (CDCl$_3$): 7.20-7.34 (m, 15H), 4.49-4.74 (m, 6H), 3.42-3.64 (m, 4H), 3.17 (d, J=11.9 Hz, 1H), 2.84 (d, J=11.9 Hz, 1H), 1.38 (s, 3H); IR (KBr) 3030, 2866, 1453, 1103, 697 cm$^{-1}$; MS (ES+) 418.44 (M+H, 100%).

Alternatively, compound 34 is prepared as per Scheme 4 from known 2-C-methyl-D-ribonic-γ-lactone, 4-1 (methods in Carbohydrate Chemistry (1963), 12, p. 484-485). Benzylation of 4-1 with benzyl bromide and sodium hydride gives perbenzylated product 4-2, which upon reduction with sodium borohydride generates open chain compound 4-3. The primary hydroxyl group is protected with TBDMS or TBDPS and the secondary hydroxyl is converted to azido through double inversion under standard conditions known in the literature to produce 4-5. The deprotection of the primary hydroxyl under acidic conditions followed by methanesulfonyl chloride reaction in the presence of a base gives 4-6, which upon reduction with TPP and water generates the desired pyrrolidine compound 3-4.

EXAMPLE 10

(2R,3R,4S)-2-(Hydroxymethyl)-4-methylpyrrolidine-3,4-diol hydrochloride (5-1, Scheme 5)

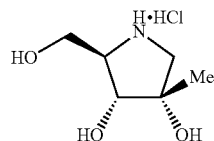

To a solution of compound 3-2 (8.7 g, 20.3 mmol) in MeOH (200 mL) is added HCl (1 N in MeOH, 101 mL, 101 mmol) followed by Pd/C (10%, 4.0 g) and the mixture hydrogenated at 60 psi for 22 h. The catalyst is removed by filtration through a short pad of Celite and the filtrate concentrated to give a white solid, which was crystallized from MeOH to afford 2.28 g (61%) of 5-1 as a white solid, mp. 216-218° C.

$^1$HNMR (CD$_3$OD): 3.72-3.92 (m, 3H), 3.48-3.50 (m, 1H), 3.22 (d, J=12.0 Hz, 1H), 3.12 (d, J=12.0 Hz, 1H), 1.32 (s, 3H); $^{13}$C NMR (CD$_3$OD): 79.18, 79.10, 67.53, 62.53, 58.23, 24.04; MS (ES+) 148.64 (M+H, 100%).

Alternative route: Compound 5-1 is also prepared through Scheme 5 from a known compound 5-2 (Tetrahedron Lett. (1997), 38, 3103-3106). The details are given below.

Step 1:

To a solution of compound 5-2 (24.6 g, 71 mmol) in methanol (280 mL) is added concentrated HCl (30 mL, 360 mmol) and the reaction mixture heated at reflux for 1 h. After cooling, the reaction mixture is concentrated and dried under high vacuum at 56° C. The dry product is dissolved in methanol (200 mL), and diisopropylethyl amine (12.37 mL, 71 mmol) is added to bring the pH of the reaction mixture to about 8 and stirred at RT for 1 h. The solid obtained is collected by filtration and washed with cold methanol (50 mL) to furnish 6.9 g (60%) of 5-3 as a white solid; mp 202-207° C.

$^1$HNMR (DMSO): δ 7.60 (s, 1H), 4.98 (s, 1H), 4.94 (d, J=7.2 Hz, 1H), 4.69 (t, J=5.3 Hz, 1H), 3.60-3.54 (ddd, J=3.3, 5.3, and 11.3 Hz, 1H), 3.45 (t, J=6.6 Hz, 1H), 3.33 (dt, J=5.5, 9.0, and 11.0 Hz, 1H), 3.21 (dt, J=3.4, 6.0, and 9.5 Hz, 1H), 1.11 (s, 3H); $^{13}$C NMR (DMSO): δ 21.94, 59.94, 61.47, 73.03, 74.01, 175.53; MS (ES$^-$) 160.56 (M$^{-1}$).

Step 2:

A mixture of the product from step 1 (6.28 g, 39 mmol), sodium sulfate (55.4 g, 39 mmol) and p-toluenesulfonic acid monohydrate (0.74 g, 3.9 mmol) in 2,2-dimethoxypropane (170 mL) is heated at 70° C. for 24 h. After cooling to RT, solid K$_2$CO$_3$ (1.62 g, 11.7 mmol) is added and stirred for 30 min. The reaction mixture is filtered through Celite and the residue washed with ethyl acetate (100 mL). To the filtrate is added triethylamine (3.8 mL, 39 mmol) and the mixture is concentrated. The residue is purified on a column of silica gel using hexanes:EtOAc (95:5 to 25:75) to provide:

1. 5-4 (5.8 g, 55%) as a white solid; mp 130-133° C.

$^1$HNMR (DMSO-d$_6$): δ 7.93 (s, 1H), 4.24 (s, 1H), 3.50 (t, J=4.0 Hz, 1H), 3.40-3.27 (m, 2H), 3.07 (s, 3H), 1.38 (s, 3H), 1.30 (s, 3H), 1.28 (s, 3H), 1.25 (s, 3H), 1.23 (s, 3H); MS (ES$^+$) 296.50 (M+Na).

2. 5-5 (1.84 g, 24%) as a white solid; mp 132-135° C.

$^1$HNMR (DMSO): δ 7.88 (bs, 1H), 5.05 (t, J=5.3 Hz, 1H), 4.25 (s, 1H), 3.47-3.41 (m, 1H), 3.34-3.28 (m, 2H), 1.35 (s, 3H), 1.30 (s, 3H), 1.28 (s, 3H); $^{13}$C NMR (DMSO): δ 20.65, 26.86, 27.43, 58.69, 62.27, 82.10, 83.17, 110.54, 175.13;. MS (ES$^+$) 202.55 (M+1).

Step 3:

To a slurry of lithium aluminum hydride (3.17 g, 83.5 mmol) in THF (167 mL) at RT is added a solution of compound 5-4 (9.1 g, 33.4 mmol) in THF (68 mL) and the reaction mixture is heated at reflux for 9 h. After cooling to 0° C., the reaction mixture is quenched carefully with water (6 mL) and diluted with ethyl acetate (400 mL). The heterogeneous reaction mixture is filtered through Celite and the residue washed with ethyl acetate (200 mL). The filtrate is concentrated and the residue purified on a column of silica gel using CMA-80 in chloroform (0 to 50%) to give 7.3 g (83%) of product 5-6 as an oil.

$^1$HNMR (CDCl$_3$): δ 4.40 (s, 1H), 3.60-3.52 (m, 2H), 3.50-3.45 (m, 1H), 3.35 (s, 3H), 3.14 (d, J=12.5 Hz, 1H), 2.96 (d, J=12.5 Hz, 1H), 2.59 (bs, 1H), 1.64 (s, 3H), 1.61 (s, 3H), 1.53 (s, 3H), 1.48 (s, 6H); $^{13}$C NMR (CDCl$_3$): δ 24.00, 24.51, 26.88, 28.08, 48.77, 60.07, 61.06, 65.80, 89.45, 90.90, 100.24, 111.37; MS (ES$^+$) 266.45 (M+Li).

Compound 5-5 is also converted to 5-7 by following the same procedure as given above for 5-6. Compound is obtained in 83% yield as an oil, which solidified on standing; mp 62-64° C.

$^1$HNMR (DMSO-d$_6$): δ 4.62 (bs, 1H), 4.12 (s, 1H), 3.37-3.21 (m, 2H), 3.01 (dd, J=7.2 and 6.2 Hz, 1H), 2.79 (d, J=11.9 Hz, 1H), 2.59 (d, J=11.9 Hz, 1H), 1.37 (s, 3H), 1.36 (s, 3H), 1.27 (s, 3H); $^{13}$C NMR (DMSO-d$_6$) δ 24.50, 28.16, 29.54, 59.19, 61.24, 67.05, 88.60, 90.10, 110.91; MS (ES$^+$) 188.57 (M$^{+1}$).

Both compounds 5-6 and 5-7 are converted to 5-1 with acid (HCl) treatment.

EXAMPLE 11

(3aS,6R,6aR)-6-((tert-Butyldimethylsilyloxy)methyl)-2,2,3a-trimethyl-tetrahydro-3aH-[1,3]dioxolo[4,5-c]pyrrole (6-5, Scheme 6)

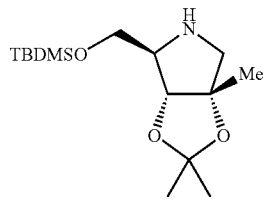

Step 1:

To a solution of the compound from example 10 (2.1 g, 11.44 mmol) in MeOH (25 mL) containing DIPEA (3.9 mL, 22.88 mmol) is added FmocCl (3.4 g, 13.16 mmol) at 0-5° C. and stirred for 1.5 h. The reaction mixture is diluted with water (150 mL), saturated with salt and extracted with CHCl$_3$:MeOH (10:3) mixture (3×100 mL). The combined organic layers are dried with Mg SO$_4$, filtered and the filtrate concentrated. The residue is purified on silica gel column using CHCl$_3$:MeOH (100:0 to 90:10) as an eluent to give 5.12 g of the corresponding Fmoc compound, 6-2. MS (ES+) 392.40 (M+Na).

Step 2:

The compound obtained in step 1 (5.00 g) is treated with acetone (70 mL), 2,2-dimethoxy propane (10 mL) and p-toluenesulfonic acid (300 mg) at RT and stirred for 16 h. The reaction mixture is concentrated and the residue is purified on a column of silica gel using hexanes:EtOAc (100:0 to 40:60) as eluent to give 4.8 g (87%) of 6-3 as a thick gum.

$^1$HNMR (DMSO): 7.89 (d, J=7.3 Hz, 2H) 7.62 (d, J=7.3 Hz, 2H) 7.39-7.43 (m, 2H) 7.29-7.34 (m, 2H) 4.99-5.06 (m, 1H), 4.18-4.43(m, 4H), 3.72-3.89 (m, 1H ), 3.62-3.68 (m, 1H), 3.19-3.55 (m, 3H), 1.45, 1.43, 1.31, 1.30 (2s, 6H), 1.29 and 1.23 (2s, 3H); MS (ES+) 432.37 (M+Na, 100%).

Step 3:

To a solution of the compound from step 2 (2.4 g, 5.86 mmol) in $CH_2Cl_2$ (200 mL) containing imidazole (1.5 g, 23.44 mmol) is added a solution of TBDMSCl (1.8 g, 11.72 mmol) in $CH_2Cl_2$ (20 mL) at RT and the reaction mixture is stirred for 1.5 h. Additional imidazole (0.75 g, 11.72 mmol) and TBDMSCl (0.9 g, 5.86 mmol) in $CH_2Cl_2$ (10 mL) are added and stirred for 1 h. The reaction mixture is washed with water (2×250 mL), dried over Mg $SO_4$, filtered and the filtrate concentrated. The residue is purified on a column of silica gel using hexanes:EtOAc (100:0 to 90:10) as eluent to give 4.2 g of the corresponding TBDMS compound, 6-4.

MS (ES+) 546.45 (M+Na, 100%).

Step 4:

A solution of 20% piperidine in THF (50 mL) is added to the compound from step 3 (4.2 g) and the mixture is stirred at RT for 15 min. After evaporation of the solvent, the residue is purified on a column of silica gel using hexanes:EtOAc:MeOH (80:20:0 to 50:50:5) as eluent to give 1.5 g of 6-5 as an oil.

$^1$HNMR (CDCl$_3$): 4.27 (d, J=1.5 Hz, 1H) 3.68 (dd, J=10.4 and 4.9 Hz, 1H) 3.59 (dd, J=10.4 and 6.0 Hz, 1H), 3.20-3.25 (m, 1H), 3.00 (d, J=12.4 Hz, 1H), 2.77 (d, J=12.4 Hz, 1H), 2.46 (brs, 1H), 1.47(s, 6H), 1.39 (s, 3H), 0.89 (s, 9H), 0.06 (s, 3H), 0.05 (s, 3H); $^{13}$C NMR (CDCl$_3$) 111.95, 90.96, 89.10, 67.62, 64.70, 60.34, 28.39, 27.25, 26.07, 21.40, 14.56; MS (ES+) 302.51 (M+H, 100%).

EXAMPLE 12

(2S,3S,4R,5R)-2-(4-Amino-5H-pyrrolo[3,2-d]pyrimidin-7-yl)-5-(hydroxymethyl)-3-methylpyrrolidine-3,4-diol (Scheme 7, 7-9)

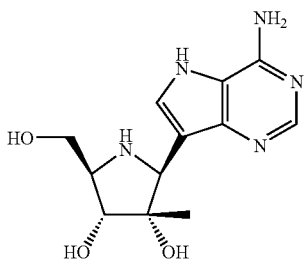

Step 1:

To a slurry of selenium dioxide (121 mg, 1.093 mmol) and compound 65 (3.3 g, 10.93 mmol) in acetone (20 mL) cooled to 0° C., is added via syringe pump hydrogen peroxide (30% aqueous, 7.5 mL) over a period of 2 h and the mixture is further stirred for 2 h. The reaction mixture is diluted with chloroform (50 mL) and washed with water (20 mL). The aqueous layer is extracted with chloroform (10 mL). The combined organic layers are washed with brine (20 mL), dried (MgSO$_4$), filtered and the filtrate is concentrated. The residue is purified on a column of silica gel using hexanes:EtOAc (95:5 to 20:80) to furnish imine 7-1 (2.521 g, 73%).

$^1$HNMR (CDCl$_3$): δ 6.84 (s, 1H), 4.54 (brs, 1H), 4.34 (dd, J=11.1 and 2.4 Hz, 1H), 3.98 (m, 1H), 3.88 (dd, J=11.1 and 2.4 Hz, 1H), 1.59 (s, 3H), 1.42 (s, 6H), 0.89 (s, 9H), 0.09 (s, 3H), 0.07 (s, 3H); $^{13}$C NMR (CDCl$_3$): δ −5.43, −5.14, 18.79, 23.24, 26.13, 27.52, 27.93, 60.29, 81.72, 82.34, 87.20 111.75, 137.13; MS (ES$^+$) 316.47 (M$^{+1}$).

Step 2:

To a solution of n-BuLi (1.6 M in hexane, 24.8 mL, 39.7 mmol) diluted with THF (100 mL) cooled to −70° C. is added dropwise acetonitrile (2.08 mL, 39.7 mmol) over a period of 5 min. The anion formed is stirred for 30 min at −70° C. and to this is added a solution of the compound from step 1 (2.5 g, 7.94 mmol) in THF (20 mL) over a period of 10 min. The reaction mixture is stirred for 2 h at −70° C. and quenched with water (30 mL). The reaction mixture is allowed to warm to RT and is further diluted with water (30 mL) and hexanes (100 mL). The aqueous layer is separated and extracted with ether:hexanes (1:1, 100 mL). The organic layers are combined and washed with brine (50 mL), dried (MgSO$_4$), filtered and the filtrate is concentrated to furnish 2.93 g of the product. To a solution of this product (2.83 g, 7.94 mmol) in acetic acid (16 mL) at RT is added zinc dust (4.76 g) and stirred at RT for 15 h. Additional acetic acid (16 mL) and zinc dust (4.7 g) are added and further stirred for 3 h, followed by the additional amounts of acetic acid (8 mL) and zinc dust (2.35 g). After stirring for 4 h, the reaction mixture is diluted with chloroform (100 mL) and filtered through a pad of Celite to remove zinc dust. The filtrate is concentrated and the residue dissolved in chloroform (50 mL) and washed with saturated aqueous NaHCO$_3$ (50 mL). The milky aqueous layer is again extracted with chloroform (25 mL). The combined organic layers are washed with brine (50 mL), dried (MgSO$_4$), filtered and the filtrate is concentrated. The residue is purified on a column of silica gel using hexanes:EtOAc (95:5 to 20:80) to furnish 1.146 g (42.5%) of pyrrolidine 7-2 as an oil.

$^1$HNMR (CDCl$_3$): δ 4.07 (d, J=2.6 Hz, 1H), 3.69 (m, 2H), 3.40 (dd, J=4.8 and 8.7 Hz, 1H), 3.35-3.31 (m, 1H), 2.57 (dd, J=4.7 and 16.5 Hz, 1H), 2.35 (dd, J=8.8 and 16.5 Hz, 1H), 1.50 (s, 3H), 1.36 (s, 3H), 1.30 (s, 3H), 0.70 (s, 9H), 0.08 (s, 6H); $^{13}$C NMR (CDCl$_3$): δ −5.56, −5.51, 18.22, 18.41, 18.54, 25.78, 26.54, 28.17, 63.01, 63.27, 64.00, 87.71, 87.78, 113.61, 117.87; MS (ES$^+$) 341.50 (M$^+$).

Step 3:

To a solution of the compound from step 2 (0.8 g, 2.36 mmol) in chloroform (25 mL) is added (Boc)$_2$O (0.78 g, 3.53 mmol) and the reaction mixture is stirred at RT for 16 h. After concentration, the residue is purified by flash column chromatography on a silica gel column using hexanes:EtOAc (95:5 to 20:80) to furnish 7-3 (0.974 g, 94%) as an oil which solidifies on standing; mp 68-71° C.

$^1$HNMR (CDCl$_3$): δ 4.41 (d, J =4.0 Hz, 1H), 4.28 (m, 1H), 4.12-3.95 (m, 1H), 3.79-3.68 (m, 2H), 2.88-2.71 (m, 2H), 1.60 (s, 3H), 1.50 (s, 9H), 1.43 (s, 6H), 0.93 (s, 9H), 0.12 (s, 6H); MS (ES$^+$) 464.08 (M+Na).

Step 4:

To a solution of the compound from step 3 (0.65 g, 1.47 mmol) in DMF (6 mL) is added Bredereck's reagent (1.2 mL 5.91 mmol) and heated at 75-80° C. for 24 h. Since the reaction is not complete, additional amounts of Bredereck's reagent (1.2 mL, 5.91 mmol) are added at every 16 h interval (3×1.2 mL). After cooling to RT, water (50 mL) is added and the mixture is extracted with toluene (2×25 mL). The combined organic layers are washed with water (25 mL), dried over MgSO$_4$, filtered and the filtrate is concentrated. The residue is purified on a column of silica gel using hexanes:EtOAc (100:0 to 90:10) to provide 0.89 g (61%) of 74 as a colorless oil.

$^1$HNMR (DMSO-d$_6$): δ 6.72 (s, 1H, olefinic proton for major isomer), 6.42 (brs, 1H, olefinic proton for minor isomer), 4.22-4.27 (m, 2H), 3.47-4.03 (m, 3H), 2.99-3.00 (m, 6H), 1.24-1.50 (m, 18H), 0.86-0.87 (m, 9H), 0.05-0.06 (m, 6H); IR (KBr) 2932, 2858, 2184, 1696, 1633, 1388, 1255, 1169, 837 cm$^{-1}$; MS (ES+) 518.54 (M+Na, 100%).

Step 5:

A solution of the compound from step 4 (0.6 g, 1.21 mmol) in a mixture of THF/H$_2$O/AcOH (30 mL, 1:1:1) is stirred for 5 h and extracted with CHCl$_3$ (2×50 mL). The combined organic layers are washed with saturated NaHCO$_3$ (2×25 mL), dried over MgSO$_4$, filtered and the filtrate is concentrated to dryness to give the corresponding enol 7-5 (0.5 g); MS (ES–) 467.46 (M–H, 100%).

Step 6:

To a solution of the compound from step 5 (0.16 g, 0.34 mmol) in MeOH (3 mL) is added aminoacetonitrile hydrochloride (0.142 g, 1.54 mmol) and sodium acetate (0.251 g, 3.07 mmol) and stirred at RT for 20 h. Additional aminoacetonitrile (0.142 g, 1.54 mmol) and sodium acetate (0.251 g, 3.07 mmol) are added and further stirred 20 h. The white solid is removed by filtration and the filtrate is concentrated and the residue is purified on a silica gel column using hexanes:EtOAc (90:10 to 80:20) to provide 0.05 g (31%) of the desired compound 7-6 as an oil.

MS (ES+) 529.44 (M+Na, 100%) and (ES–) 505.46 (M–H, 100%).

Step 7:

To a solution of the compound from step 6 (0.05 g, 0.108 mmol) in CH$_2$Cl$_2$ (5 mL) is added DBU (0.164 g, 1.08 mmol) and methyl chloroformate (0.061 g, 0.648 mmol) and then heated at reflux temperature for 18 h. Additional DBU (0.164 g, 1.08 mmol) and methyl chloroformate (0.061 g, 0.648 mmol) are added and refluxed further for 8 h. The reaction mixture is diluted with MeOH (5 mL) and stirred at RT for 2 h. The reaction is neutralized with AcOH, concentrated and the residue purified on a silica gel column using hexanes:EtOAc (90:10 to 70:30) to provide 0.015 g (27%) of the desired compound 7-7.

MS (ES+) 529.42 (M+Na, 100%) and (ES–) 505.49 (M–H, 100%).

Step 8:

A mixture of the compound from step 7 (0.015 g, 0.029 mmol) and formamidine acetate (21 mg, 0.17 mmol) in EtOH (4 mL) is heated at reflux temperature for 18 h. The reaction mixture is evaporated to dryness and the residue purified on a silica gel column using CHCl$_3$:MeOH (90:10 to 80:20) to provide 10 mg (63%) of the desired compound 7-8; MS (ES+) 534.54 (M+H, 100%) and (ES–) 532.51 (M–H, 100%).

Step 9:

A solution of the compound from step 8 (15 mg) in 1.2 N methanolic HCl (1.0 mL) is heated at 50° C. for 2 h. The reaction mixture is evaporated to dryness to get a white solid, which is washed with Et$_2$O and dried under vacuum (60° C., 3 h) to give 8.7 mg of the target 7-9 as hydrochloride.

$^1$HNMR (D$_2$O): δ 8.36 (s, 1H), 8.00 (s, 1H), 5.0 (s, 1H), 4.43 (d, J=8.6 Hz, 1H), 4.05 (m, 2H), 3.77-3.80 (m, 1H), 1.07 (s, 3H); $^{13}$C NMR (D$_2$O): δ 19.73, 57.81, 62.15, 62.79, 73.60, 79.10, 106.9, 112.70, 132.28, 138.75, 143.44, 149.36; MS (ES+) 280.47 (M+H, 100%) and (ES–) 278.45 (M–H, 100%).

The conversion of compound 3-4 to 7-9 is also done as per Scheme 8. The steps involved are essentially the same as given above from 6-5 in Scheme 7.

EXAMPLE 13

(2S,3S,4R,5R)-2-(4-Aminopyrazolo[1,5-a][1,3,5]triazin-8-yl)-5-(hydroxymethyl)pyrrolidine-3,4-diol (Scheme 9, 9-4, R'=H)

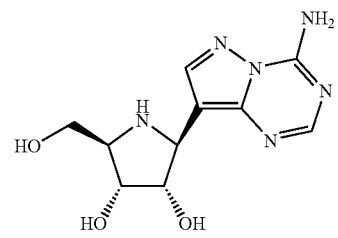

Step 1:

A mixture of compound 9-1 (2.0 g, 4.15 mmol, prepared by following the method reported in Tetrahedron (2000), 56, 3055-3062), hydrazine (3.09 mL, 9.6 mmol), hydrazine monohydrochloride (410 mg, 0.6 mmol) and water (0.5 mL) in MeOH (15 mL) is heated at 75-80° C. for 20 h. After cooling to RT and diluting with water (75 mL), the reaction mixture is extracted with CHCl$_3$ (2×50 mL). The combined organic extracts are dried over MgSO$_4$, filtered and the filtrate is concentrated. The residue is purified on a column of silica gel using hexanes:EtOAc:MeOH (100:0:0 to 50:50:5) to provide 1.8 g (84%) of the product 9-2; MS (ES+) 469 (M+H, 70%).

Step 2:

The compound from step 1 (1.3 g, 2.77 mmol) is treated with N-cyanoethylformamidate (1.08 g, 11.09 mmol) in benzene (40 mL) and the reaction mixture is heated at 75-80° C. for 3 h. After evaporation, the residue is purified twice on a silica gel column using hexanes:EtOAc (100:0 to 50:50) to provide 1.1 g (76%) of product 9-3.

$^1$HNMR (CDCl$_3$): δ 8.17 (s, 1H), 8.03 (brs, 1H), 6.76 (brs, 2H) 5.10-5.29 (m, 2H) 4.90 (brs, 1H), 4.2 (m, 1H), 3.52-3.57 (m, 2H), 1.56, 1.47, 1.39 (3s, 15H), 0.82 (s, 9H), 0.00 (s, 3H), –0.08 (s, 3H); MS (ES+) 543.42 (M+Na, 100%), (ES–) 519.45 (M–H, 100%).

Step 3:

To a solution of the compound from step 2 (1.1 g, 2.11 mmol) in MeOH (22 mL) is added concentrated HCl (2 mL) and stirred for 17 h. Additional concentrated HCl (2.0 mL) is added and the mixture is stirred for 3 h. After evaporation, the residue is purified on a column of silica gel using chloroform:methanol (80:20) to CMA-80 to provide a solid, which is washed with 50% ethyl acetate in hexanes to give 0.65 g (95%) of 9-4.

$^1$HNMR (DMSO): δ 10.3 (brs, 1H, D$_2$O exchangeable), 8.8 (brs, 1H, D$_2$O exchangeable), 8.58 (brs, 2H, D$_2$O exchangeable), 8.35 (s, 1H), 8.16 (s, 1H), 5.20-5.70 (m, 3H, D$_2$O exchangeable), 4.58-4.66(m, 1H), 4.46-4.56 (m, 1H), 4.17 (t, J=4.1 Hz, 1H), 3.70-3.75 (m, 2H), 3.44-3.54 (m, 1H); MS (ES+) 267.43 (M+H, 100%), (ES−) 265.39 (M−H, 100%).

EXAMPLE 14

(2S,3S,4R,5R)-2-(4-Aminopyrazolo[1,5-a][1,3,5]triazin-8-yl)-5-(hydroxymethyl)-3-methylpyrrolidine-3,4-diol (Scheme 9, 9-4, R'=CH$_3$)

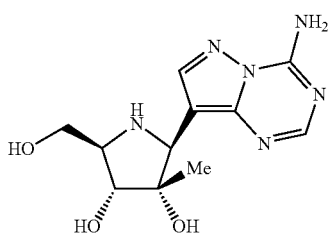

This compound is prepared from 7-5 by following the same procedures as given in example 13 (Scheme 9).

$^1$HNMR (D$_2$O): δ 8.34 (s, 1H), 8.21 (s, 1H), 5.00 (s, 1H), 4.46 (d, J=9.4 Hz, 1H), 4.06 (m, 2H), 3.75-3.84 (m, 1H), 1.12 (s, 3H); MS (ES+) 281.47 (M+H, 100%), (ES−) 279.44 (M−H, 100%).

EXAMPLE 15

((2S,5R)-5-(4-Amino-5H-pyrrolo[3,2-d]pyrimidin-7-yl)pyrrolidin-2-yl)methanol (Scheme 10, 10-9)

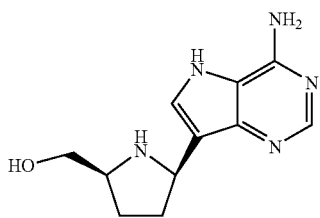

Step 1:
To (1-Benzyl-5-hydroxymethyl-pyrrolidin-2-yl)-methanol (5.74 g, 25.9 mmol, prepared by following the method reported in J. Am. Chem. Soc. (1999), 121, 432-443) in pyridine (250 mL) is added TBDPSCl (6.73 mL, 25.9 mmol) and the reaction mixture stirred for 16 h at RT. After evaporation of pyridine, the reaction mixture is partitioned between EtOAc (200 mL) and water (200 mL). The organic layer is collected, dried over MgSO$_4$, filtered and the filtrate is concentrated. The residue is purified on a column of silica gel using EtOAc:hexanes (0:100 to 20:80) to afford 2.3 g (20%) of 10-2.

Step 2:
A solution of 10-2 from step 1 in EtOH (50 mL) is treated with palladium hydroxide (20%, 2 g) and the reaction mixture hydrogenated at 100 psi for 48 h. After removing the catalyst by filtration, the filtrate is concentrated and the residue is dissolved in CHCl$_3$ (50 mL). The reaction mixture is treated with (Boc)$_2$O (1 g, 55 mmol) and stirred for 3 h at RT. After concentration, the residue is purified on a column of silica gel using EtOAc:hexanes (0:100 to 30:70) to afford 2.1 g (89%) of 10-3.

$^1$H NMR: δ 7.60 (m, 4H), 7.40 (m, 6H), 4.00 (m, 2H), 3.80-3.40 (m, 4H), 2.20-1.80 (m, 5H), 1.40 (s, 9H), 1.10 (s, 9H); MS ES$^+$ (470.23, M+H$^+$).

Step 3:
To a solution of the compound from step 2 (2.1 g, 4.4 mmol) in pyridine (50 mL) is added tosyl chloride (6.7 mmol, 1.28 g) and the reaction mixture is stirred for 16 h at RT. After evaporation of the solvent, the residue is partitioned between EtOAc (200 mL) and water (200 mL). The organic layer is collected and concentrated. The residue is purified on a silica gel column using hexanes:EtOAc (100:0 to 70:30) to give 2.5 g (90%) of tosylated product 10-4.

Step 4:
To a solution of the compound from step 3 (2.5 g, 4.06 mmol) in DMF (50 mL) is added sodium cyanide (1.0 g, 20 mmol) and the reaction mixture is stirred for 16 h at. 50° C. Additional sodium cyanide (1.0 g, 20 mmol) is added and the reaction mixture is stirred at 70° C. for 3 h. The reaction mixture is cooled and diluted with EtOAc (200 mL) and water (200 mL). The organic layer is collected, washed with water (2×200 mL) and concentrated. The residue is purified on a silica gel column using hexanes:EtOAc (100:0 to 70:30) to give 1.4 g (72%) of cyano compound 10-5.

$^1$H NMR: δ 7.60 (m, 4H), 7.30 (m, 6H), 4.00 (m, 2H), 3.60 (m, 2H), 2.60 (m,2H), 2.10 (m, 2H), 1.90 (m, 2H), 1.30 (m, 9H), 1.00 (s, 9H); MS ES$^+$ (479.34, M+H$^+$).

The conversion of cyano compound 10-5 to target 10-9 is accomplished through 10-6, 10-7, and 10-8 in the same way as given under Example 12.

$^1$H NMR (DMSO): δ 9.80 (br s, 1H), 9.00 (br s, 2H), 8.60 (s, 1H), 8.00 (s, 1H), 5.20 (m, 1H), 4.80 (m, 1H), 3.60 (m, 4H), 2.30-1.70 (m, 4H); MS ES$^+$ (234.56, M+H$^+$), MS ES− (232.52, M−H$^−$).

EXAMPLE 16

(2R,3S,5R)-2-(4-Amino-5H-pyrrolo[3,2-d]pyrimidin-7-yl)-5-(hydroxymethyl)pyrrolidin-3-ol (11-5, Scheme 11)

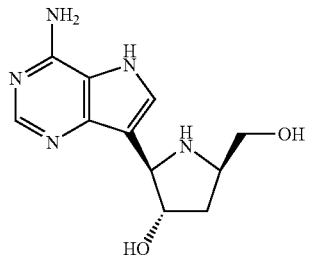

Compound 11-5 is prepared from known 3-hydroxy-5-hydroxymethylpyrrolidine (11-1, prepared by following the method reported in J. Org. Chem. (1981), 46, 2954-2960). Compound 11-1 is reacted with (Boc)$_2$O to give N-protected derivative 11-2, which upon benzylation produces dibenzylated product 11-3. Deprotection of Boc in 11-3 is achieved under acidic conditions to produce 11-4, which upon same reaction sequence as used under Scheme 7 produces the desired target 11-5;

$^1$H NMR (D$_2$O): δ 8.4 (s, 1H), 7.97 (s, 1H), 4.88 (m, 2H), 4.20 (bs, 1H), 3.93 (m, 1H), 3.81 (m, 1H), 2.43 (m, 1H), 2.30 (m, 1H); MS ES$^+$ (250.47, M+H$^+$).

EXAMPLE 17

7-((2S,3S,4R,5R)-3,4-Dihydroxy-5-(hydroxymethyl)pyrrolidin-2-yl)-2-(methylthio)-3H-pyrrolo[3,2-d]pyrimidin-4(5H)-one (12-5, Scheme 12)

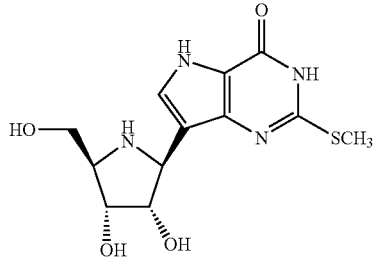

Protected derivative 12-3 is prepared according to the scheme 12 following the procedures reported in Tetrahedron (2000), 56, 3053-3062. Protected derivative on acid treatment produces the target 12-5.

$^1$H NMR (D$_2$O): δ 7.58 (s, 1H), 4.93-4.87 (m, 2H), 4.49 (t, J=4.5 Hz, 1H), 3.95 (m, 2H), 3.83 (dd, J=9.5 and 4.3 Hz, 1H); MS ES$^+$ (313.41, M+H$^+$), MS ES$^-$ (311.40, M−H$^-$).

EXAMPLE 18

2-amino-7-((2S,3S,4R,5R)-3,4-Dihydroxy-5-(hydroxymethyl)pyrrolidin-2-yl)-3H-pyrrolo[3,2-d]pyrimidin-4(5H)-one (Scheme 12, 12-6)

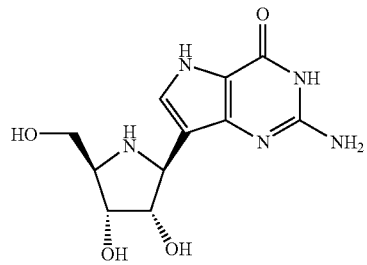

This compound is prepared according to the procedure reported in Tetrahedron (2000), 56, 3053-3062.

EXAMPLE 19

7-((2S,3S,4R,5R)-3,4-Dihydroxy-5-(hydroxymethyl)-3-methylpyrrolidin-2-yl)-3H-pyrrolo[3,2-d]pyrimidin-4(5H)-one (Scheme 13, 13-4, R=CH$_3$)

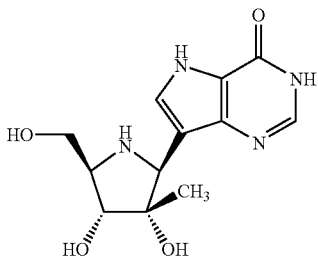

This compound is prepared from 7-5 as shown in Scheme 13 by following the same procedures as reported in Tetrahedron (2000), 56, 3053-3062.

EXAMPLE 20

(2S,3S,4R,5R)-2-(4-Aminothieno[3,2-d]pyrimidin-7-yl)-5-(hydroxymethyl)-3-methylpyrrolidine-3,4-diol (Scheme 14, 14-5, R'=CH$_3$)

(2S,3S,4R,5R)-2-(4-Aminothieno[3,2-d]pyrimidin-7-yl)-5-(hydroxymethyl)pyrrolidine-3,4-diol (Scheme 14, 14-5, R'=H)

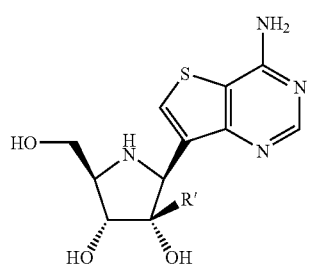

R'=H, CH$_3$

Compound 14-1, when R'=H is reported in Tetrahedron (2000), 56, 3053-3062 and compound 14-1 when R'=CH$_3$ is the same as given in Scheme 7 as 7-5. These compounds are reacted with methanesulfonyl chloride to give 14-2, which upon treatment with acetylthioacetonitrile in the presence of base generate thiophene derivatives 14-3. The isomers (α and β) are separated and the each isomer of compound 14-3 is further reacted with formamidine acetate to produce thienopyrimidine ring 14-4, which on acidic treatment is deprotected to yield the desired target 14-5, with R'=H and CH$_3$.

EXAMPLE 21

(2S,3S,4R,5R)-2-(4-Aminofuro[3,2-d]pyrimidin-7-yl)-5-(hydroxymethyl)-3-methylpyrrolidine-3,4-diol (Scheme15, 15-5, R'=CH$_3$)

(2S,3S,4R,5R)-2-(4-Aminofuro[3,2-d]pyrimidin-7-yl)-5-(hydroxymethyl)pyrrolidine-3,4-diol (Scheme 15, 15-5, R'=H)

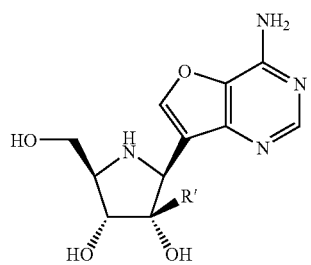

R'=H, CH$_3$

Compound 15-1, when R'=H is reported in Tetrahedron (2000), 56, 3053-3062 and compound 15-1 when R'=CH$_3$ is the same as given in Scheme 7 as 7-5. These compounds are reacted with chloroacetonitrile in the presence of KF and 18-crown-6 to give 15-2, which upon treatment with base such as LDA generate furan derivatives 15-3. The isomers (α and β) are separated and the each isomer of compound 15-3 is further reacted with formamidine acetate to produce furopyrimidine ring 15-4, which on acidic treatment is deprotected to yield the desired target 15-5, with R'=H and $CH_3$.

EXAMPLE 22

((2S,5R)-5-(4-Amino-5H-pyrrolo[3,2-d]pyrimidin-7-yl)pyrrolidin2-yl)methyl dihydrogen phosphate (Scheme 16, 16-4)

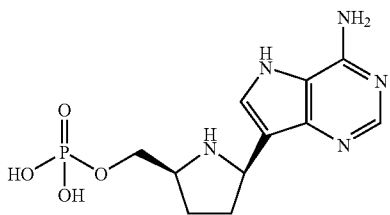

Step 1:

To a solution of compound 10-8 in Scheme 10 (0.24 g, 0.45 mmol) in pyridine (20 mL) is added triphenylmethyl chloride (0.25 g, 0.675 mmol) and the reaction mixture is stirred at 70° C. for 18 h. After evaporation, the residue is purified on a column of silica gel using EtOAc:hexanes (0:100 to 20:80) to give 0.21 g (53%) of compound 16-1.

Step 2:

The compound produced in step 1 (0.21 g, 0.24 mmol) is dissolved in THF (20 mL) and a solution of 1 M TBAF in THF (0.5 mL, 0.5 mmol) is added and the reaction mixture stirred at RT for 16 h. After evaporation, the residue is purified on a column of silica gel using $MeOH:CHCl_3$ (5:95) to give 81 mg (72%) of 16-2.

Step 3:

The compound generated in step 2 (81 mg, 0.15 mmol) in THF (20 mL) is treated with dibenzyl N,N-diisopropylphosphoroamidate (0.055 mL, 0.165 mmol,) and tetrazole (29.5 mg, 0.45 mmol), and the reaction mixture is stirred at RT for 1 h. An additional amount of phosphoramidate reagent (0.055 mL, 0.165 mmol,) is added and stirred for 1 h. The reaction mixture is then cooled to −40° C. and mCPBA (72 mg, 0.225 mmol) is added and then allowed to warm to RT, and then stirred for 2 h at RT. The reaction mixture is partitioned between EtOAc (50 mL) and water (50 mL). The organic layer is collected, dried over $MgSO_4$, filtered and the filtrate is concentrated. The residue is purified on a column of silica gel using $MeOH:CHCl_3$ (0:100 to 5:95) to give 100 mg (73%) of 16-3.

Step 4:

The compound from step 3 is dissolved in MeOH (50 mL) and palladium on carbon (10%, 50 mg) is added and hydrogenated at 50 psi at RT for 18 h. The catalyst is removed by filtration through Celite, the filtrate is concentrated and the residue is dissolved in a mixture of $CH_2Cl_2$ (2 mL) and trifluoroacetic acid (1 mL). After stirring for 1 h at RT, the reaction mixture is evaporated to dryness, co-evaporated with $CHCl_3$, then partitioned between EtOAc (50 mL) and water (50 mL). The water layer is collected and evaporated to-dryness to give 26.2 mg (73%) of the desired target 16-4.

$^1$H NMR ($D_2O$): δ 8.40 (s, 1H), 7.90 (s, 1H), 4.00 (m, 3H), 3.40 (m, 1H), 2.30 (m, 3H), 2.00 (m, 1H); $^{31}$P NMR 1.46 ppm.

HCV NS5B Polymerase Assays

The activity of compounds predicted to inhibit HCV NS5B polymerase are examined in NS5B polymerase assay using two different RNA templates. Assays with poly(A) (primer dependent) or HCV RNA templates (primer independent, includes the genomic 3'-X stem loop) are adapted from literature and modified for the purpose of screening larger number of compounds. The reaction solution contains 0.1 M Hepes (pH 7.3), 1.75 mM $MnCl_2$, 4 mM DTT, 25 μg/mL rifampicin, 400 U/mL RNasin (Promega, Madison, Wis.), 0.6 μCi $^3$H-UTP or $^3$H-GTP (Amersham, Piscataway, N.J.), 60 μg/mL NS5B. For assays using homo-polymeric templates, primer and template (0.5 μg polyA/0.05 μg oligo$U_{16}$ or 0.5 μg polyC/0.05 μg oligo$G_{16}$) are pre-annealed at 95° C. for 5 min followed by 37° C. for 10 min before their addition to the reaction. The total volume of the reaction mixture is 50 μL and incubations are at 30° C. for 2 h. Incorporation of tritium labeled RNA is determined by transferring the reaction solution to 0.8 ml of 0.1 mg/mL calf thymus DNA, the reaction products are precipitated with 0.45 mL cold 20% trichloroacetic acid solution on ice for 30 min. The labeled RNA products are collected on glass filters and washed extensively with 0.1 M acidic sodium pyrophosphate buffer and ethanol. The filter bound radioactivity is measured using a scintillation counter.

For the hetero-polymeric template, a segment of HCV RNA is labeled with biotin to allow high throughput screening of compounds. A PCR product encoding HCV genome (+strand) RNA from the 3' non-coding region (nucleotides 9850 to 9970) is first amplified from a plasmid using a forward primer (GGATCC<u>TAATACGACTCACTATAG</u>GTG-AAGATTGGGCTAACCACTCCAGG) containing a T7 promoter (underlined) and a reverse primer (GCCGGCCACAT-GATCTGCAGAGAG). This PCR product is used to prepare HCV RNA templates, which includes the 3'-X stem loop. Biotinylated HCV RNA is produced from the PCR amplified template by in vitro transcription with biotin labeled nucleotides and T7 RNA polymerase. A 120 base biotinylated HCV (+) strand RNA product is purified with phenol chloroform extraction and size exclusion chromatography. Purified RNA is precipitated with ethanol and recovered by centrifugation. The assays using HCV RNA templates included 0.1 mM unlabeled nucleotide triphosphates and are done in 96-well streptavidin-coated Flash plates (NEN, Boston, Mass.). Biotinylated HCV RNA templates (0.2 μg per well) are pre-annealed prior to adding the reaction mixture. Assays are terminated by adding 150 μL of 20 mM EDTA (pH 8.0) in phosphate buffered saline to each well. Tritium counts are monitored using a Top counter (Packard-Instrument, Meriden, Conn.). Different amounts of the test compound, typically ranging from 1 μM to 1 mM in a less than 5% of the total incubation volume, are added to measure NS5B polymerase inhibition. The same amount of solvent present in incubations containing inhibitors was added to control reactions. The $IC_{50}$ values were calculated by the following formula: % residual activity $=100/(1+[I]/IC_{50})^s$, where [I] is the inhibitor concentration and "s" is the slope of the inhibition curve.

Formulation

The compounds of the present disclosure can be administered by any conventional means available for use in conjunction with pharmaceuticals, either as individual therapeutic agents or in a combination of therapeutic agents. Example of these further therapeutic are interferon (IFN), interferon α-2a, interferon α-2b, consensus interferon (CIFN), ribavirin, amantadine, rimantadine, interleukine-12, ursodeoxycholic acid (UDCA), glycyrrhizin, and silybum marianum. They can be administered alone, but generally administered with a pharmaceutical carrier selected on the basis of the chosen route of administration and standard pharmaceutical practice.

The pharmaceutically acceptable carriers described herein, for example, vehicles, adjuvants, excipients, or diluents, are well-known to those who are skilled in the art. Typically, the pharmaceutically acceptable carrier is chemically inert to the active compounds and has no detrimental side effects or toxicity under the conditions of use. The pharmaceutically acceptable carriers can include polymers and polymer matrices.

The compounds of this disclosure can be administered by any conventional method available for use in conjunction with pharmaceuticals, either as individual therapeutic agents or in a combination of therapeutic agents.

The dosage administered will, of course, vary depending upon known factors, such as the pharmacodynamic characteristics of the particular agent and its mode and route of administration; the age, health and weight of the recipient; the nature and extent of the symptoms; the kind of concurrent treatment; the frequency of treatment; and the effect desired. A daily dosage of active ingredient can be expected to be about 0.001 to 1000 milligrams (mg) per kilogram (kg) of body weight, with the preferred dose being 0.1 to about 30 mg/kg.

Dosage forms (compositions suitable for administration) contain from about 1 mg to about 500 mg of active ingredient per unit. In these pharmaceutical compositions, the active ingredient will ordinarily be present in an amount of about 0.5-95% weight based on the total weight of the composition.

The active ingredient can be administered orally in solid dosage forms, such as capsules, tablets, and powders, or in liquid dosage forms, such as elixirs, syrups and suspensions. It can also be administered parenterally, in sterile liquid dosage forms. The active ingredient can also be administered intranasally (nose drops) or by inhalation of a drug powder mist. Other dosage forms are potentially possible such as administration transdermally, via patch mechanism or ointment.

Formulations suitable for oral administration can consist of (a) liquid solutions, such as an effective amount of the compound dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, propylene glycol, glycerin, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of the following: lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin, or sucrose and acadia, emulsions, and gels containing, in addition to the active ingredient, such carriers as are known in the art.

The compounds of the present disclosure, alone or in combination with other suitable components, can be made into aerosol formulations to be administered via inhalation. These aerosol formulations can be placed into pressurized acceptable propellants, such as dichlorodifluoromethane, propane, and nitrogen. They also may be formulated as pharmaceuticals for non-pressured preparations, such as in a nebulizer or an atomizer.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compound can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol such as poly(ethyleneglycol) 400, glycerol ketals, such as 2,2-dimethyl-1,3-dioxolane-4-methanol, ethers, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters. Suitable soaps for use in parenteral formulations include fatty alkali metal, ammonium, and triethanolamine salts, and suitable detergents include (a) cationic detergents such as, for example, dimethyldialkylammonium halides, and alkylpyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylene polypropylene copolymers, (d) amphoteric detergents such as, for example, alkyl β-aminopropionates, and 2-alkylimidazoline quaternary ammonium salts, and (e) mixtures thereof.

The parenteral formulations typically contain from about 0.5% to about 25% by weight of the active ingredient in solution. Suitable preservatives and buffers can be used in such formulations. In order to-minimize or eliminate irritation at the site of injection, such compositions may contain one or more nonionic surfactants having a hydrophile-lipophile balance (HLB) of from about 12 to about 17. The quantity of surfactant in such formulations ranges from about 5% to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol.

Pharmaceutically acceptable excipients are also well-known to those who are skilled in the art. The choice of excipient will be determined in part by the particular compound, as well as by the particular method used to administer the composition. Accordingly, there is a wide variety of suitable formulations of the pharmaceutical composition of the present disclosure. The following methods and excipients are merely exemplary and are in no way limiting. The pharmaceutically acceptable excipients preferably do not interfere with the action of the active ingredients and do not cause adverse side-effects. Suitable carriers and excipients include solvents such as water, alcohol, and propylene glycol, solid absorbants and diluents, surface active agents, suspending agent, tableting binders, lubricants, flavors, and coloring agents.

The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets. The requirements for effective pharmaceutical carriers for injectable compositions are well known to those of ordinary skill in the art. See *Pharmaceutics and Pharmacy Practice*, J. B. Lippincott Co., Philadelphia, Pa., Banker and Chalmers, Eds., 238-250 (1982) and *ASHP Handbook on Injectable Drugs,* Toissel, 4th ed., 622-630 (1986).

Formulations suitable for topical administration include lozenges comprising the active ingredient in a flavor, usually sucrose and acacia or tragacanth; pastilles comprising the active ingredient in an inert base, such as gelatin and glycerin, or sucrose and acacia; and mouthwashes comprising the active ingredient in a suitable liquid carrier; as well as creams, emulsions, and gels containing, in addition to the active ingredient, such carriers as are known in the art.

Additionally, formulations suitable for rectal administration may be presented as suppositories by mixing with a variety of bases such as emulsifying bases or water-soluble bases. Formulations suitable for vaginal administration may be presented as pessaries, tampons, creams, gels, pastes, foams, or spray formulas containing, in addition to the active ingredient, such carriers as are known in the art to be appropriate.

Suitable pharmaceutical carriers are described in Remington's Pharmaceutical Sciences, Mack Publishing Company, a standard reference text in this field.

The dose administered to an animal, particularly a human, in the context of the present disclosure should be sufficient to effect a therapeutic response in the animal over a reasonable time frame. One skilled in the art will recognize that dosage will depend upon a variety of factors including a condition of the animal, the body weight of the animal.

A suitable dose is that which will result in a concentration of the active agent in a patient which is known to effect the desired response. The size of the dose also will be determined by the route, timing and frequency of administration as well as the existence, nature, and extend of any adverse side effects that might accompany the administration of the compound and the desired physiological effect.

Useful pharmaceutical dosage forms for administration of the compounds according to the present disclosure can be illustrated as follows:

Hard Shell Capsules

A large number of unit capsules are prepared by filling standard two-piece hard gelatine capsules each with 100 mg of powdered active ingredient, 150 mg of lactose, 50 mg of cellulose and 6 mg of magnesium stearate.

Soft Gelatin Capsules

A mixture of active ingredient in a digestible oil such as soybean oil, cottonseed oil or olive oil is prepared and injected by means of a positive displacement pump into molten gelatin to form soft gelatin capsules containing 100 mg of the active ingredient. The capsules are washed and dried. The active ingredient can be dissolved in a mixture of polyethylene glycol, glycerin and sorbitol to prepare a water miscible medicine mix.

Tablets

A large number of tablets are prepared by conventional procedures so that the dosage unit was 100 mg of active ingredient, 0.2 mg. of colloidal silicon dioxide, 5 mg of magnesium stearate, 275 mg of microcrystalline cellulose, 11 mg. of starch, and 98.8 mg of lactose. Appropriate aqueous and non-aqueous coatings may be applied to increase palatability, improve elegance and stability or delay absorption.

Immediate Release Tablets/Capsules

These are solid oral dosage forms made by conventional and novel processes. These units are taken orally without water for immediate dissolution and delivery of the medication. The active ingredient is mixed in a liquid containing ingredient such as sugar, gelatin, pectin and sweeteners. These liquids are solidified into solid tablets or caplets by freeze drying and solid state extraction techniques. The drug compounds may be compressed with viscoelastic and thermoelastic sugars and polymers or effervescent components to produce porous matrices intended for immediate release, without the need of water.

Moreover, the compounds of the present disclosure can be administered in the form of nose drops, or metered dose and a nasal or buccal inhaler. The drug is delivered from a nasal solution as a fine mist or from a powder as an aerosol.

The foregoing description of the disclosure illustrates and describes the present invention. Additionally, the disclosure shows and describes only the preferred embodiments of the invention but, as mentioned above, it is to be understood that the invention is capable of use in various other combinations, modifications, and environments and is capable of changes or modifications within the scope of the inventive concept as expressed herein, commensurate with the above teachings and/or the skill or knowledge of the relevant art. The embodiments described hereinabove are further intended to explain best modes known of practicing the disclosure and to enable others skilled in the art to utilize the disclosure in such, or other, embodiments and with the various modifications required by the particular applications or uses of the disclosure. Accordingly, the description is not intended to limit the disclosure to the form disclosed herein. Also, it is intended that the appended claims be construed to include alternative embodiments.

All publications, patents and patent applications cited in this specification are herein incorporated by reference, and for any and all purposes, as if each individual publication, patent or patent application were specifically and individually indicated to be incorporated by reference. In the case of inconsistencies, the present disclosure will prevail.

What is claimed is:

1. A compound or a pharmaceutically acceptable salt thereof represented by the formula:

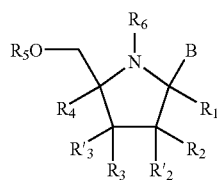

wherein,
$R_1$ is H, $CH_3$, $C_2H_5$, or $C_3H_7$;
$R_2$ is H, $CH_3$, $C_2H_5$, $C_3H_7$, $CH=CH_2$, $CH_2-OH$, $CH_2F$, or $CF_3$;
$R'_2$ is OH, $NH_2$, NH-alkyl, F, $N_3$, $OCH_3$, or O—C(O)CH($NH_2$)alkyl;
$R_3$ is H, $CH_3$, $C_2H_5$, or $C_3H_7$;
$R'_3$ is H, OH, $NH_2$, NH-alkyl, F, $N_3$, $OCH_3$, or O—C(O)CH($NH_2$)alkyl;
$R_4$ is H, $CH_3$, $C_2H_5$, or $C_3H_7$;
at least one of $R_2$, $R_3$, and $R_4$ has to be other than H, when X=NH in B

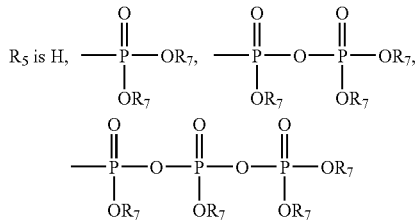

$R_6$ is H or

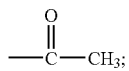

$R_7$ is selected from H, alkyl, alkenyl, aryl, acyloxyalkyl, and pivaloyloxyalkyl, aminoacids, and $CH_2CH_2SC(O)$alkyl;
B is represented by the following structure:

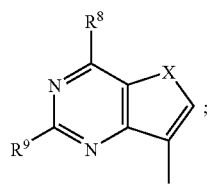

X is $NR^6$, O, or S;
$R^8$ is H, $NH_2$, OH, SH, F, Cl, Br, I, aryl, heterocycle, alkyl, alkene, alkyne, S-alkyl, S-aryl, S(O)-alkyl, $SO_2$-alkyl, $SO_2NH_2$, $SO_2NH$-alkyl, $SO_2NH$-aryl, NH-alkyl, NH-aryl, N(alkyl)$_2$, N(aryl)$_2$, O-alkyl, O-aryl, O-heterocycle, $NH-(CH_2)_n$-aryl, NH—C(O)-alkyl, or NH—C(O)-aryl; and
$R_9$ is H, $NH_2$, OH, SH, F, Cl, Br, I, aryl, heterocycle, alkyl, alkene, alkyne, S-alkyl, S-aryl, S(O)-alkyl, $SO_2$-alkyl, $SO_2NH_2$, $SO_2NH$-alkyl, $SO_2NH$-aryl, NH-alkyl, NH-aryl, N(alkyl)$_2$, N(aryl)$_2$, O-alkyl, O-aryl, O-heterocycle, $NH-(CH_2)_n$-aryl, NH—C(O)-alkyl, or NH—C(O)-aryl.

2. A compound selected from the group consisting of:
(2R,3R,4S,5S)-2-(Hydroxymethyl)-5-(4-(methoxyamino)-5H-pyrrolo[3,2-d]pyrimidin-7-yl)pyrimidine-3,4-diol,
(2R,3R,4S,5S)-2-(Hydroxymethyl)-5-(4-(1-methylhydrazinyl)-5H-pyrrolo[3,2-d]pyrimidin-7-yl)pyrrolidine-3,4-diol,
(2S,3S,4R,5R)-2-(4-(1-Ethylhydrazinyl)-5H-pyrrolo[3,2-d]pyrimidin-7-yl)-5-(hydroxymethyl)pyrimidine-3,4-diol,
(2S,3S,4R,5R)-2-(4-(Dimethylamino)-5H-pyrrolo[3,2-d]pyrimidin-7-yl)-5-(hydroxymethyl)pyrromidine-3,4-diol,
(2R,3R,4R)-3,4-Bis(benzyloxy)-2-(benzyloxymethyl)-4-methylpyrrolidine,
(2R,3R,4S)-3,4-Bis(benzyloxy)-2-(benzyloxymethyl)-4-methylpyrrolidine,
(2R,3R,4S)-2-(Hydroxymethyl)-4-methylpyrrolidine-3,4-diol hydrochloride,
(3aS,6R,6aR)-6-((tert-Butyldimethylsilyloxy)methyl)-2,2,3a-trimethyl-tetrahydro-3aH-[1,3]dioxolo[4,5-c]pyrrole,
(2S,3S,4R,5R)-2-(4-Amino-5H-pyrrolo[3,2-d]pyrimidin-7-yl)-5-(hydroxymethyl)-3-methylpyrrolidine-3,4-diol,
(2S,3S,4R,5R)-2-(4-Aminopyrazolo[1,5-a][1,3,5]triazin-8-yl)-5-(hydroxymethyl)pyrrolidine-3,4-diol,
(2S,3S,4R,5R)-2-(4-Aminopyrazolo[1,5-a][1,3,5]triazin-8-yl)-5-(hydroxymethyl)-3-methylpyrrolidine-3,4-diol,
7-((2S,3S,4R,5R)-3,4-Dihydroxy-5-(hydroxymethyl)pyrrolidin-2-yl)-2-(methylthio)-3H-pyrrolo[3,2-d]pyrimidin-4(5H)-one,
7-((2S,3S,4R,5R)-3,4-Dihydroxy-5-(hydroxymethyl)-3-methylpyrrolidin-2-yl)-3H-pyrrolo[3,2-d]pyrimidin-4(5H)-one,
(2S,3S,4R,5R)-2-(4-Aminothieno[3,2-d]pyrimidin-7-yl)-5-(hydroxymethyl)-3-methylpyrrolidine-3,4-diol,
(2S,3S,4R,5R)-2-(4-Aminofuro[3,2-d]pyrimidin-7-yl)-5-(hydroxymethyl)-3-methylpyrrolidine-3,4-diol, and
((2S,5R)-5-(4-Amino-5H-pyrrolo[3,2-d]pyrimidin-7-yl)pyrrolidin-2-yl)methyl dihydrogen phosphate.

3. A pharmaceutical composition comprising a compound according to any one of claims 1 and 2, and a pharmaceutical carrier.

4. A method for inhibiting RNA viral polymerase comprising administering to a patient in need thereof an effective amount of at least one compound according to any one of claims 1 and 2.

5. A method for inhibiting HCV polymerase comprising administering to a patient in need thereof an effective amount of at least one compound according to any one of claims 1 and 2.

6. A method for inhibiting HBV polymerase comprising administering to a patient in need thereof an effective amount of at least one compound according to any one of claims 1 and 2.

7. A method for inhibiting Rhino polymerase comprising administering to a patient in need thereof an effective amount of at least one compound according to any one of claims 1 and 2.

8. A method for inhibiting small pox polymerase comprising administering to a patient in need thereof an effective amount of at least one compound according to any one of claims 1 and 2.

9. A method for inhibiting Ebola polymerase comprising administering to a patient in need thereof in an effective amount of at least one compound according to any one of claims 1 and 2.

10. A method for inhibiting polio virus polymerase comprising administering to a patient in need thereof an effective amount of at least one compound according to any one of claims 1 and 2.

11. A method for inhibiting West Nile polymerase comprising administering to a patient in need thereof an effective amount of at least one compound according to any one of claims 1 and 2.

12. A method for inhibiting Coxsackie A polymerase comprising administering to a patient in need thereof an effective amount of at least one compound according to any one of claims 1 and 2.

13. A method for inhibiting Coxsackie B polymerase comprising administering to a patient in need thereof an effective amount of at least one compound according to any one of claims 1 and 2.

14. A method for inhibiting Echo polymerase comprising administering to a patient in need thereof an effective amount of at least one compound according to any one of claims 1 and 2.

15. A method for treating a patient suffering from an RNA viral infection comprising administering said patient an effective amount of at least one compound according to any one of the claims 1 and 2.

16. A method for treating a patient suffering from HCV infection comprising administering to said patient an effective amount of at least one compound according to any one of the claims 1 and 2.

17. A method for treating a patient suffering from HBV infection comprising administering to said patient an effective amount of at least one compound according to any one of the claims 1 and 2.

18. A method for treating a patient suffering from a Rhino viral infection comprising administering to said patient an effective amount of at least one compound according to any one of the claims 1 and 2.

19. A method for treating a patient suffering from a small pox viral infection comprising administering to said patient an effective amount of at least one compound according to any one of the claims 1 and 2.

20. A method for treating a patient suffering from a Ebola viral infection comprising administering to said patient an effective amount of at least one compound according to any one of the claims 1 and 2.

21. A method for treating a patient suffering from a polio viral infection comprising administering to said patient an effective amount of at least one compound according to any one of the claims 1 and 2.

22. A method for treating a patient suffering from a West Nile viral infection comprising administering to said patient an effective amount of at least one compound according to any one of the claims 1 and 2.

23. A method for treating a patient suffering from a Coxsackie A viral infection comprising administering to said patient an effective amount of at least one compound according to any one of the claims 1 and 2.

24. A method for treating a patient suffering from a Coxsackie B viral infection comprising administering to said patient an effective amount of at least one compound according to any one of the claims 1 and 2.

25. A method for treating a patient suffering from an Echo viral infection comprising administering to said patient an effective amount of at least one compound according to any one of the claims 1 and 2.

26. A method for inhibiting in a patient RNA viral polymerase comprising administering to a patient in need thereof an effective amount of at least one compound according to any one of claims 1 and 2 and at least one further therapeutic agent related from the group consisting of interferon (IFN), interferon α-2a, interferon α-2b, consensus interferon (CIFN), ribavirin, amantadine, rimantadine, interleukine-12, ursodeoxycholic acid (UDCA), and glycyrrhizin, and inhibiting RNA viral polymerase.

27. The method of claim 26 wherein the RNA viral polymerase comprises at least one member selected from the group consisting of HCV polymerase, HBV polymerase, Rhino polymerase, small pox virus polymerase, Ebola virus polymerase, Coxsackie A and B polymerase, Echo polymerase and west Nile virus polymerase.

28. A method for treating RNA viral infection comprising administering to a patient in need thereof an effective amount of at least one compound according to any one of claims 1 and 2 and at least one further therapeutic agent chosen from interferon (IFN), interferon α-2a, interferon α-2b, consensus interferon (CIFN), ribavirin, amantadine, rimantadine, interleukine-12, ursodeoxycholic acid (UDCA), and glycyrrhizin.

29. The method of claim 28 wherein the RNA viral infection comprises at least one member selected from the group consisting of HCV, HBV, Coxsackie A, Coxsackie B, Echo, Rhino viral infection, small pox viral infection, Ebola viral infection, polio viral infection and West Nile viral infection.

* * * * *